(12) United States Patent
Davalos et al.

(10) Patent No.: US 8,992,517 B2
(45) Date of Patent: Mar. 31, 2015

(54) IRREVERSIBLE ELECTROPORATION TO TREAT ABERRANT CELL MASSES

(75) Inventors: Rafael V. Davalos, Blacksburg, VA (US); Paulo A. Garcia, Christianburg, VA (US); John H. Rossmeisl, Blacksburg, VA (US); John L. Robertson, Floyd, VA (US); Robert E. Neal, Richmond, VA (US)

(73) Assignee: Virginia Tech Intellectual Properties Inc., Blacksburg, VA (US)

( * ) Notice: Subject to any disclaimer, the term of this patent is extended or adjusted under 35 U.S.C. 154(b) by 511 days.

(21) Appl. No.: 12/491,151

(22) Filed: Jun. 24, 2009

(65) Prior Publication Data

US 2010/0030211 A1    Feb. 4, 2010

Related U.S. Application Data

(63) Continuation-in-part of application No. 12/432,295, filed on Apr. 29, 2009.

(60) Provisional application No. 61/125,840, filed on Apr. 29, 2008, provisional application No. 61/171,564, filed on Apr. 22, 2009, provisional application No. 61/167,997, filed on Apr. 9, 2009, provisional application No. 61/075,216, filed on Jun. 24, 2008.

(51) Int. Cl.
| | |
|---|---|
| *A61B 18/14* | (2006.01) |
| *A61N 1/32* | (2006.01) |
| *C12N 13/00* | (2006.01) |
| *A61N 1/05* | (2006.01) |

(52) U.S. Cl.
CPC ............... *A61N 1/327* (2013.01); *C12N 13/00* (2013.01); *A61N 1/05* (2013.01)
USPC ............................................. 606/41; 606/32

(58) Field of Classification Search
USPC .............. 606/27–37, 41, 42, 48–50; 607/101, 607/102, 116; 604/20–22; 128/898
See application file for complete search history.

(56) References Cited

U.S. PATENT DOCUMENTS

| | | |
|---|---|---|
| 1,653,819 A | 12/1927 | Northcott et al. |
| 4,016,886 A | 4/1977 | Doss |
| 4,226,246 A | 10/1980 | Fragnet |
| 4,262,672 A | 4/1981 | Kief |
| 4,407,943 A | 10/1983 | Cole et al. |
| 4,416,276 A | 11/1983 | Newton et al. |
| 4,810,963 A | 3/1989 | Blake-Coleman et al. |

(Continued)

FOREIGN PATENT DOCUMENTS

| | | |
|---|---|---|
| DE | 863111 | 1/1953 |
| DE | 863111tr | 1/1953 |

(Continued)

OTHER PUBLICATIONS

Co-pending U.S. Appl. No. 12/757,901, filed Apr. 9, 2010.

(Continued)

*Primary Examiner* — Michael Peffley
(74) *Attorney, Agent, or Firm* — New River Valley IP Law; Michele L. Mayberry

(57) ABSTRACT

The present invention provides methods, devices, and systems for in vivo treatment of cell proliferative disorders. The invention can be used to treat solid tumors, such as brain tumors. The methods rely on non-thermal irreversible electroporation (IRE) to cause cell death in treated tumors.

31 Claims, 23 Drawing Sheets

(56) References Cited

U.S. PATENT DOCUMENTS

| | | |
|---|---|---|
| 4,822,470 A | 4/1989 | Chang |
| 4,907,601 A | 3/1990 | Frick |
| 4,946,793 A | 8/1990 | Marshall, III |
| 5,019,034 A | 5/1991 | Weaver et al. |
| 5,052,391 A | 10/1991 | Silberstone et al. |
| 5,058,605 A | 10/1991 | Slovak |
| 5,098,843 A | 3/1992 | Calvin |
| 5,134,070 A | 7/1992 | Casnig |
| 5,173,158 A | 12/1992 | Schmukler |
| 5,192,312 A | 3/1993 | Orton |
| 5,193,537 A | 3/1993 | Freeman |
| 5,273,525 A | 12/1993 | Hofmann |
| 5,283,194 A | 2/1994 | Schmukler |
| 5,318,563 A | 6/1994 | Malis et al. |
| 5,328,451 A | 7/1994 | Davis et al. |
| 5,389,069 A | 2/1995 | Weaver |
| 5,403,311 A | 4/1995 | Abele et al. |
| 5,425,752 A | 6/1995 | Vu'Nguyen |
| 5,439,440 A | 8/1995 | Hofmann |
| 5,458,625 A | 10/1995 | Kendall |
| 5,533,999 A | 7/1996 | Hood et al. |
| 5,536,240 A | 7/1996 | Edwards et al. |
| 5,575,811 A | 11/1996 | Reid et al. |
| 5,626,146 A | 5/1997 | Barber et al. |
| 5,634,899 A | 6/1997 | Shapland et al. |
| 5,674,267 A | 10/1997 | Mir et al. |
| 5,702,359 A | 12/1997 | Hofmann |
| 5,718,246 A | 2/1998 | Vona |
| 5,720,921 A | 2/1998 | Meserol |
| 5,778,894 A | 7/1998 | Dorogi et al. |
| 5,782,882 A | 7/1998 | Lerman et al. |
| 5,800,378 A | 9/1998 | Edwards et al. |
| 5,810,762 A | 9/1998 | Hofmann |
| 5,836,905 A | 11/1998 | Lemelson et al. |
| 5,843,026 A | 12/1998 | Edwards et al. |
| 5,843,182 A | 12/1998 | Goldstein |
| 5,873,849 A | 2/1999 | Bernard |
| 5,919,142 A | 7/1999 | Boone et al. |
| 5,947,889 A | 9/1999 | Hehrlein |
| 5,983,131 A | 11/1999 | Weaver et al. |
| 5,991,697 A | 11/1999 | Nelson et al. |
| 5,999,847 A | 12/1999 | Elstrom |
| 6,009,347 A | 12/1999 | Hofmann |
| 6,010,613 A | 1/2000 | Walters et al. |
| 6,016,452 A | 1/2000 | Kasevich |
| 6,029,090 A | 2/2000 | Herbst |
| 6,041,252 A | 3/2000 | Walker et al. |
| 6,055,453 A | 4/2000 | Hofmann et al. |
| 6,068,650 A | 5/2000 | Hofmann et al. |
| 6,085,115 A | 7/2000 | Weaver et al. |
| 6,090,106 A | 7/2000 | Goble et al. |
| 6,102,885 A | 8/2000 | Bass |
| 6,106,521 A | 8/2000 | Blewett et al. |
| 6,109,270 A | 8/2000 | Mah et al. |
| 6,122,599 A | 9/2000 | Mehta |
| 6,132,419 A | 10/2000 | Hofmann |
| 6,159,163 A | 12/2000 | Strauss et al. |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann |
| 6,219,577 B1 | 4/2001 | Brown et al. |
| 6,241,702 B1 | 6/2001 | Lundquist et al. |
| 6,241,725 B1 * | 6/2001 | Cosman ................ 606/41 |
| 6,261,831 B1 | 7/2001 | Agee |
| 6,278,895 B1 | 8/2001 | Bernard |
| 6,300,108 B1 | 10/2001 | Rubinsky |
| 6,326,177 B1 | 12/2001 | Schoenbach et al. |
| 6,347,247 B1 | 2/2002 | Dev et al. |
| 6,349,233 B1 | 2/2002 | Adams |
| 6,351,674 B2 | 2/2002 | Silverstone |
| 6,387,671 B1 | 5/2002 | Rubinsky et al. |
| 6,403,348 B1 | 6/2002 | Rubinsky et al. |
| 6,470,211 B1 | 10/2002 | Ideker et al. |
| 6,482,619 B1 | 11/2002 | Rubinsky et al. |
| 6,493,592 B1 | 12/2002 | Leonard et al. |
| 6,500,173 B2 | 12/2002 | Underwood et al. |
| 6,526,320 B2 | 2/2003 | Mitchell |
| 6,562,604 B2 | 5/2003 | Rubinsky et al. |
| 6,607,529 B1 | 8/2003 | Jones et al. |
| 6,611,706 B2 | 8/2003 | Avrahami et al. |
| 6,613,211 B1 | 9/2003 | McCormick et al. |
| 6,627,421 B1 | 9/2003 | Unger et al. |
| 6,653,091 B1 | 11/2003 | Dunn et al. |
| 6,669,691 B1 | 12/2003 | Taimisto |
| 6,678,558 B1 | 1/2004 | Dimmer et al. |
| 6,692,493 B2 | 2/2004 | McGovern et al. |
| 6,697,669 B2 | 2/2004 | Dev et al. |
| 6,697,670 B2 | 2/2004 | Chornenky et al. |
| 6,702,808 B1 | 3/2004 | Kreindel |
| 6,795,728 B2 | 9/2004 | Chornenky et al. |
| 6,801,804 B2 | 10/2004 | Miller et al. |
| 6,865,416 B2 | 3/2005 | Dev et al. |
| 6,892,099 B2 | 5/2005 | Jaafar et al. |
| 6,912,417 B1 | 6/2005 | Bernard et al. |
| 6,927,049 B2 * | 8/2005 | Rubinsky et al. ......... 435/173.7 |
| 6,962,587 B2 | 11/2005 | Johnson et al. |
| 6,972,014 B2 | 12/2005 | Eum et al. |
| 6,994,706 B2 | 2/2006 | Chornenky et al. |
| 7,053,063 B2 | 5/2006 | Rubinsky et al. |
| 7,054,685 B2 | 5/2006 | Dimmer et al. |
| 7,063,698 B2 | 6/2006 | Whayne et al. |
| 7,113,821 B1 | 9/2006 | Sun et al. |
| 7,130,697 B2 | 10/2006 | Chornenky et al. |
| 7,211,083 B2 | 5/2007 | Chornenky et al. |
| 7,267,676 B2 | 9/2007 | Chornenky et al. |
| 7,344,533 B2 | 3/2008 | Pearson et al. |
| 7,655,004 B2 * | 2/2010 | Long ................ 606/37 |
| 7,674,249 B2 | 3/2010 | Ivorra et al. |
| 7,680,543 B2 * | 3/2010 | Azure ................ 607/115 |
| 7,718,409 B2 | 5/2010 | Rubinsky et al. |
| 7,951,582 B2 | 5/2011 | Gazit et al. |
| 7,955,827 B2 | 6/2011 | Rubinsky et al. |
| 8,048,067 B2 | 11/2011 | Davalos et al. |
| 8,114,070 B2 | 2/2012 | Rubinsky et al. |
| 8,162,918 B2 | 4/2012 | Ivorra et al. |
| 8,282,631 B2 | 10/2012 | Davalos et al. |
| 8,298,222 B2 | 10/2012 | Rubinsky et al. |
| 8,348,921 B2 | 1/2013 | Ivorra et al. |
| 8,425,505 B2 | 4/2013 | Long |
| 8,465,484 B2 | 6/2013 | Davalos et al. |
| 8,518,031 B2 | 8/2013 | Boyden et al. |
| 8,603,087 B2 | 12/2013 | Rubinsky et al. |
| 8,835,166 B2 | 9/2014 | Phillips et al. |
| 8,926,606 B2 | 1/2015 | Davalos et al. |
| 2001/0044596 A1 | 11/2001 | Jaafar |
| 2001/0046706 A1 | 11/2001 | Rubinsky et al. |
| 2001/0051366 A1 | 12/2001 | Rubinsky et al. |
| 2002/0010491 A1 | 1/2002 | Schoenbach et al. |
| 2002/0055731 A1 | 5/2002 | Atala et al. |
| 2002/0077676 A1 | 6/2002 | Schroeppel et al. |
| 2002/0082543 A1 | 6/2002 | Park et al. |
| 2002/0099323 A1 | 7/2002 | Dev et al. |
| 2002/0115208 A1 | 8/2002 | Mitchell et al. |
| 2002/0119437 A1 | 8/2002 | Grooms |
| 2002/0137121 A1 | 9/2002 | Rubinsky et al. |
| 2002/0138117 A1 | 9/2002 | Son |
| 2002/0183684 A1 | 12/2002 | Dev et al. |
| 2002/0193831 A1 | 12/2002 | Smith, III |
| 2003/0009110 A1 | 1/2003 | Tu et al. |
| 2003/0060856 A1 | 3/2003 | Chornenky et al. |
| 2003/0088189 A1 | 5/2003 | Tu et al. |
| 2003/0096407 A1 | 5/2003 | Atala |
| 2003/0130711 A1 | 7/2003 | Pearson et al. |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0199050 A1 | 10/2003 | Mangano et al. |
| 2003/0208200 A1 | 11/2003 | Palanker et al. |
| 2003/0225360 A1 | 12/2003 | Eppstein et al. |
| 2004/0009459 A1 | 1/2004 | Anderson et al. |
| 2004/0019371 A1 | 1/2004 | Jaafar et al. |
| 2004/0059389 A1 | 3/2004 | Chornenky et al. |
| 2004/0146877 A1 | 7/2004 | Diss et al. |

(56) References Cited

U.S. PATENT DOCUMENTS

| | | | |
|---|---|---|---|
| 2004/0153057 A1 | 8/2004 | Davison | |
| 2004/0176855 A1 | 9/2004 | Badylak | |
| 2004/0193097 A1 | 9/2004 | Hofmann et al. | |
| 2004/0236376 A1 | 11/2004 | Miklavcic et al. | |
| 2004/0243107 A1 | 12/2004 | Mackoviak | |
| 2004/0267189 A1 | 12/2004 | Mavor et al. | |
| 2005/0013870 A1 | 1/2005 | Freyman et al. | |
| 2005/0043726 A1 | 2/2005 | McHale et al. | |
| 2005/0049541 A1 | 3/2005 | Behar et al. | |
| 2005/0165393 A1 | 7/2005 | Eppstein | |
| 2005/0171523 A1* | 8/2005 | Rubinsky et al. | 606/34 |
| 2005/0171574 A1* | 8/2005 | Rubinsky et al. | 607/2 |
| 2005/0182462 A1 | 8/2005 | Chornenky et al. | |
| 2005/0261672 A1 | 11/2005 | Deem et al. | |
| 2005/0282284 A1 | 12/2005 | Rubinsky et al. | |
| 2005/0288730 A1 | 12/2005 | Deem et al. | |
| 2006/0004356 A1 | 1/2006 | Bilski et al. | |
| 2006/0015147 A1 | 1/2006 | Persson et al. | |
| 2006/0024359 A1 | 2/2006 | Walker et al. | |
| 2006/0025760 A1 | 2/2006 | Podhajsky | |
| 2006/0079883 A1 | 4/2006 | Elmouelhi et al. | |
| 2006/0121610 A1 | 6/2006 | Rubinsky et al. | |
| 2006/0142801 A1 | 6/2006 | Demarais et al. | |
| 2006/0212078 A1 | 9/2006 | Demarais et al. | |
| 2006/0217703 A1 | 9/2006 | Chornenky et al. | |
| 2006/0235474 A1 | 10/2006 | Demarais | |
| 2006/0264752 A1* | 11/2006 | Rubinsky et al. | 600/439 |
| 2006/0264807 A1 | 11/2006 | Westersten et al. | |
| 2006/0269531 A1 | 11/2006 | Beebe et al. | |
| 2006/0293713 A1* | 12/2006 | Rubinsky et al. | 607/2 |
| 2006/0293725 A1* | 12/2006 | Rubinsky et al. | 607/72 |
| 2006/0293730 A1 | 12/2006 | Rubinsky et al. | |
| 2006/0293731 A1* | 12/2006 | Rubinsky et al. | 607/98 |
| 2007/0021803 A1 | 1/2007 | Deem | |
| 2007/0025919 A1 | 2/2007 | Deem et al. | |
| 2007/0043345 A1* | 2/2007 | Davalos et al. | 606/32 |
| 2007/0060989 A1* | 3/2007 | Deem et al. | 607/99 |
| 2007/0118069 A1 | 5/2007 | Persson et al. | |
| 2007/0129711 A1 | 6/2007 | Altshuler et al. | |
| 2007/0156135 A1 | 7/2007 | Rubinsky et al. | |
| 2007/0230757 A1 | 10/2007 | Trachtenberg et al. | |
| 2007/0287950 A1 | 12/2007 | Kjeken et al. | |
| 2008/0015571 A1 | 1/2008 | Rubinsky et al. | |
| 2008/0021371 A1 | 1/2008 | Rubinsky et al. | |
| 2008/0033340 A1 | 2/2008 | Heller et al. | |
| 2008/0033417 A1 | 2/2008 | Nields et al. | |
| 2008/0045880 A1 | 2/2008 | Kjeken et al. | |
| 2008/0052786 A1 | 2/2008 | Lin et al. | |
| 2008/0071262 A1* | 3/2008 | Azure | 606/34 |
| 2008/0097422 A1 | 4/2008 | Edwards et al. | |
| 2008/0103529 A1 | 5/2008 | Schoenbach et al. | |
| 2008/0132884 A1 | 6/2008 | Rubinsky et al. | |
| 2008/0132885 A1 | 6/2008 | Rubinsky et al. | |
| 2008/0200912 A1 | 8/2008 | Long | |
| 2008/0214986 A1 | 9/2008 | Ivorra et al. | |
| 2008/0269586 A1 | 10/2008 | Rubinsky et al. | |
| 2009/0024075 A1 | 1/2009 | Schroeppel | |
| 2009/0029407 A1 | 1/2009 | Gazit et al. | |
| 2009/0062788 A1 | 3/2009 | Long et al. | |
| 2009/0105703 A1 | 4/2009 | Shadduck | |
| 2009/0198231 A1 | 8/2009 | Esser et al. | |
| 2009/0247933 A1 | 10/2009 | Maor et al. | |
| 2009/0248012 A1 | 10/2009 | Maor et al. | |
| 2009/0269317 A1 | 10/2009 | Davalos | |
| 2009/0281477 A1 | 11/2009 | Mikus et al. | |
| 2009/0292342 A1 | 11/2009 | Rubinsky et al. | |
| 2009/0318905 A1 | 12/2009 | Bhargav et al. | |
| 2009/0326436 A1 | 12/2009 | Rubinsky et al. | |
| 2010/0023004 A1 | 1/2010 | Francischelli et al. | |
| 2010/0030211 A1 | 2/2010 | Davalos et al. | |
| 2010/0049190 A1 | 2/2010 | Long et al. | |
| 2010/0057074 A1 | 3/2010 | Roman et al. | |
| 2010/0087813 A1 | 4/2010 | Long | |
| 2010/0130975 A1 | 5/2010 | Long | |
| 2010/0152725 A1 | 6/2010 | Pearson et al. | |
| 2010/0160850 A1 | 6/2010 | Ivorra et al. | |
| 2010/0179530 A1 | 7/2010 | Long et al. | |
| 2010/0196984 A1 | 8/2010 | Rubinsky et al. | |
| 2010/0204560 A1 | 8/2010 | Salahieh et al. | |
| 2010/0204638 A1 | 8/2010 | Hobbs et al. | |
| 2010/0249771 A1 | 9/2010 | Pearson et al. | |
| 2010/0250209 A1 | 9/2010 | Pearson et al. | |
| 2010/0255795 A1 | 10/2010 | Rubinsky et al. | |
| 2010/0256630 A1 | 10/2010 | Hamilton, Jr. et al. | |
| 2010/0261994 A1 | 10/2010 | Davalos et al. | |
| 2010/0331758 A1 | 12/2010 | Davalos et al. | |
| 2011/0034209 A1 | 2/2011 | Rubinsky et al. | |
| 2011/0106221 A1 | 5/2011 | Neal, II et al. | |
| 2011/0118732 A1 | 5/2011 | Rubinsky et al. | |
| 2011/0217730 A1 | 9/2011 | Gazit et al. | |
| 2012/0034131 A1 | 2/2012 | Rubinsky et al. | |
| 2012/0071872 A1 | 3/2012 | Rubinsky et al. | |
| 2012/0071874 A1 | 3/2012 | Davalos et al. | |
| 2012/0089009 A1 | 4/2012 | Omary et al. | |
| 2012/0109122 A1 | 5/2012 | Arena et al. | |
| 2012/0179091 A1 | 7/2012 | Ivorra et al. | |
| 2012/0226218 A1 | 9/2012 | Phillips et al. | |
| 2012/0277741 A1 | 11/2012 | Davalos et al. | |
| 2013/0090646 A1 | 4/2013 | Moss et al. | |
| 2013/0108667 A1 | 5/2013 | Soikum et al. | |
| 2013/0184702 A1 | 7/2013 | Neal, II et al. | |
| 2013/0196441 A1 | 8/2013 | Rubinsky et al. | |
| 2013/0197425 A1 | 8/2013 | Golberg et al. | |
| 2013/0202766 A1 | 8/2013 | Rubinsky et al. | |
| 2013/0253415 A1 | 9/2013 | Sano et al. | |
| 2013/0281968 A1 | 10/2013 | Davalos et al. | |
| 2013/0345779 A1 | 12/2013 | Maor et al. | |
| 2014/0088578 A1 | 3/2014 | Rubinsky et al. | |
| 2014/0163551 A1 | 6/2014 | Maor et al. | |

FOREIGN PATENT DOCUMENTS

| | | |
|---|---|---|
| DE | 4000893 | 7/1991 |
| DE | 4000893tr | 7/1991 |
| EP | 0378132 | 7/1990 |
| EP | 0935482 A | 8/1999 |
| EP | 0935482 | 5/2005 |
| EP | 0935482 B1 | 5/2005 |
| WO | 9639531 | 12/1996 |
| WO | 9814238 A | 4/1998 |
| WO | 0020554 | 4/2000 |
| WO | 0107583 | 2/2001 |
| WO | 0107584 | 2/2001 |
| WO | 0107585 | 2/2001 |
| WO | 0110319 A | 2/2001 |
| WO | WO 01/10319 | 2/2001 |
| WO | WO 01/48153 | 7/2001 |
| WO | 0181533 | 11/2001 |
| WO | WO 02/078527 | 10/2002 |
| WO | 02089686 A | 11/2002 |
| WO | WO 02/089686 | 11/2002 |
| WO | 02100459 A | 12/2002 |
| WO | WO 02/100459 | 12/2002 |
| WO | 03099382 A | 12/2003 |
| WO | WO 03/099382 | 12/2003 |
| WO | 2004037341 | 5/2004 |
| WO | 2005065284 A | 7/2005 |
| WO | 2009134876 A | 11/2009 |
| WO | 2010118387 A1 | 10/2010 |
| WO | 2010151277 A | 12/2010 |
| WO | 2011047387 A | 4/2011 |
| WO | 2012071526 A | 5/2012 |
| WO | 2012088149 A | 6/2012 |

OTHER PUBLICATIONS

Co-pending U.S. Appl. No. 12/609,779, filed Oct. 30, 2009.
Beneken and Thevenia (eds) IOS Press pp. 165-173 (1993).
PCT International Preliminary Report on Patentability from PCT/US2010/030629 dated Oct. 11, 2011.
Amasha, et al., Quantitative Assessment of Impedance Tomography for Temperature Measurements in Microwave Hyperthermia, *Clin. Phys. Physiol. Meas.*, 1998, Suppl. A, 49-53.

(56) References Cited

OTHER PUBLICATIONS

Andreason, Electroporation as a Technique for the Transfer of Macromolecules into Mammalian Cell Lines, *J. Tiss. Cult. Meth.*, 15:56-62, 1993.

Baker, et al., Calcium-Dependent Exocytosis in Bovine Adrenal Medullary Cells with Leaky Plasma Membranes, *Nature*, vol. 276, pp. 620-622, 1978.

Barber, Electrical Impedance Tomography Applied Potential Tomography, Advances in Biomedical Engineering, Beneken and Thevenin, eds., IOS Press, 1993.

Beebe, S.J., et al., Nanosecond pulsed electric field (nsPEF) effects on cells and tissues: apoptosis induction and tumor growth inhibition. PPPS-2001 Pulsed Power Plasma Science 2001, $28^{th}$ IEEE International Conference on Plasma Science and $13^{th}$ IEEE International Pulsed Power Conference, Digest of Technical Papers (Cat. No. 01CH37251). IEEE, Part vol. 1, 2001, pp. 211-215, vol. I, Piscataway, NJ, USA.

Blad, et al., Impedance Spectra of Tumour Tissue in Comparison with Normal Tissue; a Possible Clinical Application for Electrical Impedance Tomography, *Physiol. Meas.* 17 (1996) A105-A115.

Brown, S.G., Phototherapy of tumors. *World J. Surgery*, 1983. 7: p. 700-9.

BPH Management Strategies: Improving Patient Satisfaction, *Urology Times*, May 2001, vol. 29, Supplement 1.

Brown, et al., Blood Flow Imaging Using Electrical Impedance Tomography, *Clin. Phys. Physiol. Meas.*, 1992, vol. 13, Suppl. A, 175-179.

Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.

Coates, C.W.,et al., "The Electrical Discharge of the Electric Eel, Electrophorous Electricus," Zoologica, 1937, 22(1), pp. 1-32.

Cook, et al., ACT3: A High-Speed, High-Precision Electrical Impedance Tomograph, *IEEE Transactions on Biomedical Engineering*, vol. 41, No. 8, Aug. 1994.

Cowley, Good News for Boomers, *Newsweek*, Dec. 30, 1996/Jan. 6, 1997.

Cox, et al., Surgical Treatment of Atrial Fibrillation: A Review, *Europace* (2004) 5, S20-S-29.

Crowley, Electrical Breakdown of Biomolecular Lipid Membranes as an Electromechanical Instability, *Biophysical Journal*, vol. 13, pp. 711-724, 1973.

Davalos, et al., Tissue Ablation with Irreversible Electroporation, *Annals of Biomedical Engineering*, vol. 33, No. 2, Feb. 2005.

Davalos, et al., Theoretical Analysis of the Thermal Effects During In Vivo Tissue Electroporation, Bioelectrochemistry, vol. 61, pp. 99-107, 2003.

Davalos, et al., A Feasibility Study for Electrical Impedance Tomography as a Means to Monitor Tissue Electroporation for Molecular Medicine, *IEEE Transactions on Biomedical Engineering*, vol. 49, No. 4, Apr. 2002.

Davalos, Real-Time Imaging for Molecular Medicine through Electrical Impedance Tomography of Electroporation, Dissertation for Ph.D in Engineering-Mechanical Engineering, Graduate Division of University of California, Berkeley, 2002.

Dean, Nonviral Gene Transfer to Skeletal, Smooth, and Cardiac Muscle in Living Animals, *Am J. Physiol Cell Physiol* 289: 233-245, 2005.

Dev, et al., Sustained Local Delivery of Heparin to the Rabbit Arterial Wall with an Electroporation Catheter, *Catheterization and Cardiovascular Diagnosis*, Nov. 1998, vol. 45, No. 3, pp. 337-343.

Dev, et al., Medical Applications of Electroporation, *IEEE Transactions of Plasma Science*, vol. 28, No. 1, pp. 206-223, Feb. 2000.

Duraiswami, et al., Boundary Element Techniques for Efficient 2-D and 3-D Electrical Impedance Tomography, *Chemical Engineering Science*, vol. 52, No. 13, pp. 2185-2196, 1997.

Duraiswami, et al., Efficient 2D and 3D Electrical Impedance Tomography Using Dual Reciprocity Boundary Element Techniques, *Engineering Analysis with Boundary Elements* 22, (1998) 13-31.

Duraiswami, et al., Solution of Electrical Impedance Tomography Equations Using Boundary Element Methods, *Boundary Element Technology XII*, 1997, pp. 226-237.

Edd, J., et al., In-Vivo Results of a New Focal Tissue Ablation Technique: Irreversible Electroporaton, *IEEE Trans. Biomed. Eng.* 53 (2006) p. 1409-1415.

Erez, et al., Controlled Destruction and Temperature Distributions in Biological Tissues Subjected to Monoactive Electrocoagulation, *Transactions of the ASME: Journal of Mechanical Design*, vol. 102, Feb. 1980.

Foster, R.S., et al., High-intensity focused ultrasound in the treatment of prostatic disease. *Eur. Urol.*, 1993. 23: 44-7).

Fox, et al., Sampling Conductivity Images via MCMC, Mathematics Department, Auckland University, New Zealand, May 1997.

Gauger, et al., A Study of Dielectric Membrane Breakdown in the Fucus Egg, *J. Membrane Biol.*, vol. 48, No. 3, pp. 249-264, 1979.

Gehl, et al., In Vivo Electroporation of Skeletal Muscle: Threshold, Efficacy and Relation to Electric Field Distribution, *Biochimica et Biphysica Acta* 1428, 1999, pp. 233-240.

Gençer, et al., Electrical Impedance Tomography: Induced-Current Imaging Achieved with a Multiple Coil System, *IEEE Transactions on Biomedical Engineering*, vol. 43, No. 2, Feb. 1996.

Gilbert, et al., Novel Electrode Designs for Electrochemotherapy, *Biochimica et Biophysica Acta* 1334, 1997, pp. 9-14.

Gilbert, et al., The Use of Ultrasound Imaging for Monitoring Cryosurgery, Proceedings $6^{th}$ Annual Conference, IEEE Engineering in Medicine and Biology, 107-111, 1984.

Glidewell, et al., The Use of Magnetic Resonance Imaging Data and the Inclusion of Anisotropic Regions in Electrical Impedance Tomography, *Biomed, Sci. Instrum.* 1993; 29: 251-7.

Gothelf, et al., Electrochemotherapy: Results of Cancer Treatment Using Enhanced Delivery of Bleomycin by Electroporation, *Cancer Treatment Reviews* 2003: 29: 371-387.

Griffiths, et al., A Dual-Frequency Electrical Impedance Tomography System, *Phys. Med. Biol.*, 1989, vol. 34, No. 10, pp. 1465-1476.

Griffiths, The Importance of Phase Measurement in Electrical Impedance Tomography, *Phys. Med. Biol.*, 1987, vol. 32, No. 11, pp. 1435-1444.

Griffiths, Tissue Spectroscopy with Electrical Impedance Tomography: Computer Simulations, *IEEE Transactions on Biomedical Engineering*, vol. 42, No. 9, Sep. 1995.

Gumerov, et al., The Dipole Approximation Method and Its Coupling with the Regular Boundary Element Method for Efficient Electrical Impedance Tomography, *Boundary Element Technology XIII*, 1999.

Hapala, Breaking the Barrier: Methods for Reversible Permeabilization of Cellular Membranes, *Critical Reviews in Biotechnology*, 17(2): 105-122, 1997.

Heller, et al., Clinical Applications of Electrochemotherapy, *Advanced Drug Delivery Reviews*, vol. 35, pp. 119-129, 1999.

Ho, et al., Electroporation of Cell Membranes: A Review, *Critical Reviews in Biotechnology*, 16(4): 349-362, 1996.

Holder, et al., Assessment and Calibration of a Low-Frequency System for Electrical Impedance Tomography (EIT), Optimized for Use in Imaging Brain Function in Ambulant Human Subjects, *Annals of the New York Academy of Science*, vol. 873, Issue 1, Electrical BI, pp. 512-519, 1999.

Huang, et al., Micro-Electroporation: Improving the Efficiency and Understanding of Electrical Permeabilization of Cells, *Biomedical Microdevices*, vol. 2, pp. 145-150, 1999.

Hughes, et al., An Analysis of Studies Comparing Electrical Impedance Tomography with X-Ray Videofluoroscopy in the Assessment of Swallowing, *Physiol. Meas.* 15, 1994, pp. A199-A209.

Issa, et al., The TUNA Procedure for BPH: Review of the Technology: The TUNA Procedure for BPH: Basic Procedure and Clinical Results, Reprinted from *Infections in Urology*, Jul./Aug. 1998 and Sep./Oct. 1998.

Ivanuša, et al., MRI Macromolecular Contrast Agents as Indicators of Changed Tumor Blood Flow, *Radiol. Oncol.* 2001; 35(2): 139-47.

Jaroszeski, et al., In Vivo Gene Delivery by Electroporation, *Advanced Drug Delivery Review*, vol. 35, pp. 131-137, 1999.

(56) References Cited

OTHER PUBLICATIONS

Kinosita, et al., Hemolysis of Human Erythrocytes by a Transient Electric Field, *Proc. Natl. Acad. Sci. USA*, vol. 74, No. 5, pp. 1923-1927, 1977.

Liu, et al., Measurement of Pharyngeal Transit Time by Electrical Impedance Tomography, *Clin. Phys. Physiol. Meas.*, 1992, vol. 13, Suppl. A, pp. 197-200.

Lundqvist, et al., Altering the Biochemical State of Individual Cultured Cells and Organelles with Ultramicroelectrodes, *Proc. Natl. Acad. Sci. USA*, vol. 95, pp. 10356-10360, Sep. 1998.

Lurquin, Gene Transfer by Electroporation, *Molecular Biotechnology*, vol. 7, 1997.

Lynn, et al., A New Method for the Generation and Use of Focused Ultrasound in Experimental Biology, *The Journal of General Physiology*, vol. 26, 179-193, 1942.

Miklavčič, et al., A Validated Model of an in Vivo Electric Field Distribution in Tissues for Electrochemotherapy and for DNA Electrotransfer for Gene Therapy, *Biochimica et Biophysica Acta* 1523 (2000), pp. 73-83.

Miklavčič, et al., The Importance of Electric Field Distribution for Effective in Vivo Electroporation of Tissues, *Biophysical Journal*, vol. 74, May 1998, pp. 2152-2158.

Miller, L., et al., Cancer cells ablation with irreversible electroporation, *Technology in Cancer Research and Treatment* 4 (2005) 699-706.

Mir, Therapeutic Perspectives of In Vivo Cell Electropermeabilization, *Bioelectrochemistry*, vol. 53, pp. 1-10, 2000.

Mir, L.M., et al., Electric Pulse-Mediated Gene Delivery to Various Animal Tissues, in Advances in Genetics, Academic Press, 2005, p. 83-114.

Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.

Mir, et al., Effective Treatment of Cutaneous and Subcutaneous Malignant Tumours by Electrochemotherapy, *British Journal of Cancer*, vol. 77, No. 12, pp. 2336-2342, 1998.

Mir, et al., Electrochemotherapy Potentiation of Antitumour Effect of Bleomycin by Local Electric Pulses, *European Journal of Cancer*, vol. 27, No. 1, pp. 68-72, 1991.

Mir, et al., Electrochemotherapy, a Novel Antitumor Treatment: First Clinical Trial, *C.R. Acad. Sci. Paris*, Ser. III, vol. 313, pp. 613-618, 1991.

Narayan, et al., Establishment and Characterization of a Human Primary Prostatic Adenocarcinoma Cell Line (ND-1), *The Journal of Urology*, vol. 148, 1600-1604, Nov. 1992.

Naslund, Michael J., Transurethral Needle Ablation of the Prostate, *Urology*, vol. 50, No. 2, Aug. 1997.

Naslund, Cost-Effectiveness of Minimally Invasive Treatments and Transurethral Resection (TURP) in Benign Prostatic Hyperplasia (BPH), (Abstract), Presented at 2001 AUA National Meeting Anaheim, CA, Jun. 5, 2001.

Neumann, et al., Gene Transfer into Mouse Lyoma Cells by Electroporation in High Electric Fields, *J. EMBO.*, vol. 1, No. 7, pp. 841-845, 1982.

Neumann, et al., Permeability Changes Induced by Electric Impulses in Vesicular Membranes, *J. Membrane Biol.*, vol. 10, pp. 279-290, 1972.

Okino, et al., Effects of High-Voltage Electrical Impulse and an Anticancer Drug on In Vivo Growing Tumors, *Japanese Journal of Cancer Research*, vol. 78, pp. 1319-1321, 1987.

Onik, et al., Sonographic Monitoring of Hepatic Cryosurgery in an Experimental Animal Model, *AJR American J. of Roentgenology*, vol. 144, pp. 1043-1047, May 1985.

Onik, et al., Ultrasonic Characteristics of Frozen Liver, *Cryobiology*, vol. 21, pp. 321-328, 1984.

Organ, L.W., Electrophysiological principles of radiofrequency lesion making, *Appl. Neurophysiol.*, 1976. 39: p. 69-76.

Piñero, et al., Apoptotic and Necrotic Cell Death Are Both Induced by Electroporation in HL60 Human Promyeloid Leukaemia Cells, *Apoptosis*, vol. 2, No. 3, 330-336, Aug. 1997.

Rols, M.P., et al., Highly Efficient Transfection of Mammalian Cells by Electric Field Pulses: Application to Large Volumes of Cell Culture by Using a Flow System, *Eur. J. Biochem.* 1992, 206, pp. 115-121.

Rubinsky, B., ed, Cryosurgery. *Annu Rev. Biomed.* Eng. vol. 2 2000. 157-187.

Sersa, et al., Reduced Blood Flow and Oxygenation in SA-1 Tumours after Electrochemotherapy with Cisplatin, *British Journal of Cancer*, 87, 1047-1054, 2002.

Sersa, et al., Tumour Blood Flow Modifying Effects of Electrochemotherapy: a Potential Vascular Targeted Mechanism, *Radiol. Oncol.*, 37(1): 43-8, 2003.

Sharma, et al., Poloxamer 188 Decreases Susceptibility of Artificial Lipid Membranes to Electroporation, *Biophysical Journal*, vol. 71, No. 6, pp. 3229-3241, Dec. 1996.

Shiina, S., et al, Percutaneous ethanol injection therapy for hepatocellular carcinoma: results in 146 patients. *AJR*, 1993, 160: p. 1023-8.

Thompson, et al., To determine whether the temperature of 2% lignocaine gel affects the initial discomfort which may be associated with its instillation into the male urethra, *BJU International* (1999), 84, 1035-1037.

Weaver, Electroporation: A General Phenomenon for Manipulating Cells and Tissues, *Journal of Cellular Biochemistry*, 51: 426-435, 1993.

Weaver, et al., Theory of Electroporation: A Review, *Bioelectrochemistry and Bioenergetics*, vol. 41, pp. 136-160, 1996.

Zimmermann, et al., Dielectric Breakdown of Cell Membranes, *Biophysical Journal*, vol. 14, No. 11, pp. 881-899, 1974.

Zlotta, et al., Possible Mechanisms of Action of Transurethral Needle Ablation of the Prostate on Benign Prostatic Hyperplasia Symptoms: a Neurohistochemical Study, Reprinted from *Journal of Urology*, vol. 157, No. 3, Mar. 1997, pp. 894-899.

Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.

Al-Sakere, B. et al., 2007, "Tumor ablation with irreversible electroporation." PLoS ONE 2.

Davalos, R.V. et al., 2005, "Tissue ablation with irreversible electroporation." Annals of Biomedical Engineering, 3 (2):223-231.

Edd, J.F, et al., 2007, "Mathematical modeling of irreversible electroporation for treatment planning.", Technology in Cancer Research and Treatment., 6:275-286.

Garcia et al., "Irreversible electroporation (IRE) to treat brain cancer." ASME Summer Bioengineering Conference, Marco Island, FL, Jun. 25-29, 2008.

PCT International Preliminary Report on Patentability for PCT/US2009/042100, dated Nov. 2, 2010 (7 pages).

PCT International Search Report for PCT/US2009/042100, dated Jul. 9, 2009 (1 page).

PCT International Search Report for PCT/US2009/062806, dated Jan. 19, 2010.

PCT International Search Report for PCT/US2010/030629 (WO 20101118387), dated Jul. 15, 2010.

Tekle, Ephrem, R. Dean Astumian, and P. Boon Chock, Electroporation by using bipolar oscillating electric field: An improved method for DNA transfection of NIH 3T3 cells, Proc. Natl. Acad. Sci., vol. 88, pp. 4230-4234, May 1991, Biochemistry.

Co-Pending U.S. Appl. No. 12/432,295, filed Apr. 29, 2009.
Co-Pending Application No. PCT/US04/43477, filed Dec. 21, 2004.
Co-Pending Application No. PCT/US09/42100, filed Apr. 29, 2009.
Co-Pending Application No. PCT/US09/62806, filed Oct. 30, 2009.
Co-Pending Application No. PCT/US10/30629, filed Apr. 9, 2010.
Co-Pending Application No. PCT/US11/32067, filed Nov. 23, 2011.
Co-Pending Application No. PCT/US11/66239, filed Dec. 20, 2011.
Co-Pending U.S. Appl. No. 12/491,151, filed Jun. 24, 2009.
Co-Pending U.S. Appl. No. 13/332,133, filed Dec. 20, 2011.
Mir et al., "Mechanisms of Electrochemotherapy" Advanced Drug Delivery Reviews 35:107-118 (1999).

(56) References Cited

OTHER PUBLICATIONS

PCT Written Opinion for PCT/US09/62806, dated Jan. 10, 2010, 5pgs.

Agerholm-Larsen, B., et al., "Preclinical Validation of Electrochemotherapy as an Effective Treatment for Brain Tumors", Cancer Research 71: 3753-3762 (2011).

Appelbaum, L., et al., "US Findings after Irreversible Electroporation Ablation: Radiologic-Pathologic Correlation" Radiology 262(1), 117-125 (2012).

Arena, Christopher B., et al., "Towards the development of latent heat storage electrodes for electroporation-based therapies", Applied Physics Letters, 101, 083902 (2012).

Arena, Christopher B., et al.,"Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.

Bagla, S. and Papadouris, D., "Percutaneous Irreversible Electroporation of Surgically Unresectable Pancreatic Cancer: A Case Report" J. Vascular Int. Radiol. 23(1), 142-145 (2012).

Bancroft, et al., Design of a Flow Perfusion Bioreactor System for Bone Tissue-Engineering Applications, Tissue Engineering, vol. 9, No. 3, 2003, p. 549-554.

Ben-David, E.,et al., "Characterization of Irreversible Electroporation Ablation in In Vivo Procine Liver" Am. J. Roentgenol. 198(1), W62-W68 (2012).

Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).

Co-Pending U.S. Appl. No. 12/432,295, Non-Final Office Action dated Nov. 26, 2013, 15 pages.

Co-Pending U.S. Appl. No. 13/919,640, Notice of Allowance dated Nov. 25, 2013, 15 pages.

Corovic, S., et al., "Analytical and numerical quantification and comparison of the local electric field in the tissue for—different electrode configurations," Biomed Eng Online, 6, 2007.

Daud, A.I., et al., "Phase I Trial of Interleukin-12 Plasmid Electroporation in Patients With Metastatic Melanoma," Journal of Clinical Oncology, 26, 5896-5903, Dec. 20, 2008.

Davalos, R.V., et al., "Electrical impedance tomography for imaging tissue electroporation," IEEE Transactions on Biomedical Engineering, 51, 761-767, 2004.

Demirbas, M. F., "Thermal Energy Storage and Phase Change Materials: An Overview" Energy Sources Part B 1(1), 85-95 (2006).

Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).

Faroja, M., et al., "Irreversible Electroporation Ablation: Is the entire Damage Nonthermal?", Radiology, 266(2), 462-470 (2013).

Foster RS, "High-intensity focused ultrasound in the treatment of prostatic disease", European Urology, 1993, vol. 23 Suppl 1, pp. 29-33.

Foster, R.S., et al., Production of Prostatic Lesions in Canines Using Transrectally Administered High-Intensity Focused Ultrasound. Eur. Urol., 1993; 23: 330-336.

Garcia P.A., et al., "7.0-T Magnetic Resonance Imaging Characterization of Acute Blood-Brain-Barrier Disruption Achieved with Intracranial Irreversible Electroporation", PLOS ONE, Nov. 2012, 7:11, e50482.

Garcia P.A., et al., "Pilot study of irreversible electroporation for intracranial surgery", Conf Proc IEEE Eng Med Biol Soc, 2009:6513-6516, 2009.

Garcia PA, Rossmeisl JH, Jr., Neal RE, 2nd, Ellis TL, Davalos RV, "A Parametric Study Delineating Irreversible Electroporation from Thermal Damage Based on a Minimally Invasive Intracranial Procedure", Biomed Eng Online 10: 34 (2011).

Garcia, P. A., et al., "Towards a predictive model of electroporation-based therapies using pre-pulse electrical measurements," Conf Proc IEEE Eng Med Biol Soc, vol. 2012, pp. 2575-2578, 2012.

Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" Technol. Cancer Res. Treatment 10(1), 73-83 (2011).

Hjouj, M., et al., "Electroporation-Induced BBB Disruption and Tissue Damage Depicted by MRI", Neuro-Oncology 13: Issue suppl 3, abstract ET-32 (2011).

Hjouj, M., et al., "MRI Study on Reversible and Irreversible Electroporation Induced Blood Brain Barrier Disruption", PLOS ONE, Aug. 2012, 7:8, e42817.

Lee, E.W., et al., "Imaging guided percutaneous irreversible electroporation: ultrasound and immunohistological correlation", Technol Cancer Res Treat 6: 287-294 (2007).

Li, W., et al., "The Effects of Irreversible Electroporation (IRE) on Nerves" PloS One, Apr. 2011, 6(4), e18831.

Mahmood, F., et al., "Diffusion-Weighted MRI for Verification of Electroporation-Based Treatments", Journal of Membrane Biology 240: 131-138 (2011).

Mahnic-Kalamiza, S., et al., "Educational application for visualization and analysis of electric field strength in multiple electrode electroporation," BMC Med Educ, vol. 12, p. 102, 2012.

Marty, M., et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006.

Neal II, R. E., et al., "Experimental characterization and numerical modeling of tissue electrical conductivity during pulsed electric fields for irreversible electroporation treatment planning," IEEE Trans Biomed Eng., vol. 59:4, pp. 1076-1085. Epub 2012 Jan. 6, 2012.

Neal II, R. E., et al., "Successful Treatment of a Large Soft Tissue Sarcoma with Irreversible Electroporation", Journal of Clinical Oncology, 29:13, e372-e377 (2011).

Rubinsky, B., et al., "Irreversible Electroporation: A New Ablation Modality—Clinical Implications" Technol. Cancer Res. Treatment 6(1), 37-48 (2007).

Salford, L.G., et al., "A new brain tumour therapy combining bleomycin with in vivo electropermeabilization", Biochem. Biophys. Res. Commun., 194(2): 938-943 (1993).

Sharma, A. , et al., "Review on Thermal Energy Storage with Phase Change Materials and Applications", Renewable Sustainable Energy Rev. 13(2), 318-345 (2009).

Thomson, K. R., et al., "Investigation of the Safety of Irreversible Electroporation in Humans" J. Vascular Int. Radiol. 22 (5), 611-621 (2011).

Co-Pending U.S. Appl. No. 12/432,295, Non-Final Rejection dated Nov. 10, 2011, 10 pages.

Co-Pending U.S. Appl. No. 12/432,295, Requirement for Restriction/Election dated Aug. 9, 2011, 7 pages.

Co-Pending U.S. Appl. No. 12/432,295, Response to Non-Final Rejection dated Jan. 23, 2012, 9 pages.

Co-Pending U.S. Appl. No. 12/432,295, Response to Requirement for Restriction/Election dated Sep. 2, 2011, 2 pages.

Co-Pending U.S. Appl. No. 12/609,779, Final Rejection dated Oct. 26, 2012, 20 pages.

Co-Pending U.S. Appl. No. 12/609,779, Non-Final Rejection dated May 23, 2012, 17 pages.

Co-Pending U.S. Appl. No. 12/609,779, Notice of Allowance dated Feb. 12, 2013, 7 pages.

Co-Pending U.S. Appl. No. 12/609,779, Notice of Allowance dated May 23, 2013, 2 pages.

Co-Pending U.S. Appl. No. 12/609,779, Response to Non-Final Rejection dated Sep. 24, 2012, 37 pages.

Co-Pending U.S. Appl. No. 12/609,779, Response with RCE to Final Rejection dated Dec. 18, 2012, 20 pages.

Co-Pending U.S. Appl. No. 12/757,901, Final Rejection dated Oct. 2, 2013, 11 pages.

Co-Pending U.S. Appl. No. 12/757,901, Non-Final Rejection dated Mar. 11, 2013, 12 pages.

Co-Pending U.S. Appl. No. 12/757,901, Response to Non-Final Rejection dated Aug. 12, 2013, 11 pages.

Co-Pending U.S. Appl. No. 12/906,923, filed Oct. 18, 2010.

(56) References Cited

OTHER PUBLICATIONS

Co-Pending Application No. PCT/US10/53077, filed Oct. 18, 2010.
Co-Pending Application No. PCT/US11/62067, filed Nov. 23, 2011.
Co-Pending U.S. Appl. No. 13/919,640, filed Jun. 17, 2013.
Co-Pending U.S. Appl. No. 13/958,152, filed Aug. 2, 2013.
Co-Pending U.S. Appl. No. 13/989,175, filed May 23, 2013.
Co-Pending U.S. Appl. No. 14/012,832, filed Aug. 28, 2013.
Co-Pending U.S. Appl. No. 14/017,210, filed Sep. 3, 2013.
Co-pending European Application No. 10 824 248.8, Invitation Pursuant to rule 62a(1) EPC (Sep. 25, 2013).
International Preliminary Report on Patentability of Corresponding International Application No. PCT/2011/062067, dated May 28, 2013.
Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.
Co-pending U.S. Appl. No. 10/571,162, filed Oct. 18, 2006 (published as 2007/0043345 on Feb. 22, 2007).
Co-Pending U.S. Appl. No. 12/432,295, Final Office Action dated Mar. 21, 2012, 13 pages.
Co-Pending Application No. 12/432,295, Response to Final Office Action dated Jul. 23, 2012, 10 pages.
Co-Pending U.S. Appl. No. 13/550,307, filed Jul. 16, 2012.
Extended European Search Report. May 11, 2012. PCT/US2009042100 from EP 09739678.2.
Gilbert, T. W., et al., "Decellularization of tissues and organs", Biomaterials, Elsevier Science Publishers, Barking, GB, vol. 27, No. 19, Jul. 1, 2006, pp. 3675-3683.
Maor et al., The Effect of Irreversible Electroporation on Blood Vessels, Tech. in Cancer Res. and Treatment, vol. 6, No. 4, Aug. 2007, pp. 307-312.
Maor, E., A. Ivorra, and B. Rubinsky, Non Thermal Irreversible Electroporation: Novel Technology for Vascular Smooth Muscle Cells Ablation, PLoS ONE, 2009, 4(3): p. e4757.
Maor, E., A. Ivorra, J. Leor, and B. Rubinsky, Irreversible electroporation attenuates neointimal formation after angioplasty, IEEE Trans Biomed Eng, 2008, 55(9): p. 2268-74.
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.
PCT International Search Report (Aug. 2, 2011), Written Opinion (Aug. 2, 2011), and International Preliminary Report on Patentability (Apr. 17, 2012) of PCT/US10/53077.
PCT International Search Report (Aug. 26, 2005), Written Opinion (Aug. 26, 2005), and International Preliminary Report on Patentability (Jun. 26, 2006) of PCT/US2004/043477.
PCT International Search Report (Jan. 19, 2010), Written Opinion (Jan. 19, 2010), and International Preliminary Report on Patentability (Jan. 4, 2010) of PCT/US09/62806, 15 pgs.
PCT International Search Report (Jul. 9, 2009), Written Opinion (Jul. 9, 2009), and International Preliminary Report on Patentability (Nov. 2, 2010) of PCT/US2009/042100.
PCT International Search Report and Written Opinion (Jul. 25, 2012) of PCT/US2011/062067.
Rajagopal, V. and S.G. Rockson, Coronary restenosis: a review of mechanisms and management, The American Journal of Medicine, 2003, 115(7): p. 547-553.
Rubinsky, B., "Irreversible Electroporation in Medicine", Technology in Cancer Research and Treatment, vol. 6, No. 4, Aug. 1, 2007, pp. 255-259.

Sano, M. B., et al., "Towards the creation of decellularized organ constructs using irreversible electroporation and active mechanical perfusion", Biomedical Engineering Online, Biomed Central LTD, London, GB, vol. 9, No. 1, Dec. 10, 2010, p. 83.
Schmukler, Impedance Spectroscopy of Biological Cells, Engineering in Medicine and Biology Society, Engineering Advances: New Opportunities for Biomedical Engineers, Proceedings of the 16th Annual Internal Conference of the IEEE, vol. 1, p. A74, downloaded from IEEE Xplore website, 1994.
VIDAMED, Inc., Transurethral Needle Ablation (TUNA): Highlights from Worldwide Clinical Studies, Vidamed's Office TUNA System, 2001.
PCT International Search Report (Aug. 22, 2012), and Written Opinion (Aug. 22, 2012) of PCT/US11/66239.
Co-Pending U.S. Appl. No. 12/906,923, Requirement for Restriction/Election, dated Jan. 29, 2014, 9 pages.
Boone, K., Barber, D. & Brown, B. Review—Imaging with electricity: report of the European Concerted Action on Impedance Tomography. J. Med. Eng. Technol. 21, 201-232 (1997).
Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).
Garcia, P. et al. Intracranial nonthermal irreversible electroporation: in vivo analysis. J Membr Biol 236, 127-136 (2010).
International Preliminary Report on Patentability of Corresponding International Application No. PCT/2011/066239, dated Jun. 25, 2013.
Jossinet et al., Electrical Impedance Endo-Tomography: Imaging Tissue From Inside, IEEE Transactions on Medical Imaging, vol. 21, No. 6, Jun. 2002, pp. 560-565.
Lee, E. W. et al. Advanced Hepatic Ablation Technique for Creating Complete Cell Death : Irreversible Electroporation. Radiology 255, 426-433, doi:10.1148/radiol.10090337 (2010).
Pavselj, N. et al. The course of tissue permeabilization studied on a mathematical model of a subcutaneous tumor in small animals. IEEE Trans Biomed Eng 52, 1373-1381 (2005).
Phillips, M., Maor, E. & Rubinsky, B. Non-Thermal Irreversible Electroporation for Tissue Decellularization. J. Biomech. Eng, doi:10.1115/1.4001882 (2010).
Sel, D. et al. Sequential finite element model of tissue electropermeabilization. IEEE Transactions on Biomedical Engineering 52, 816-827, doi:10.1109/tbme.2005.845212 (2005).
Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).
Weaver, J. C., Electroporation of biological membranes from multicellular to nano scales, IEEE Trns. Dielectr. Electr. Insul. 10, 754-768 (2003).
Co-Pending U.S. Appl. No. 12/432,295, Response to Non-Final Office Action, dated Apr. 28, 2014, 14 pages.
Co-Pending U.S. Appl. No. 12/906,923, Response to Restriction Requirement, dated Mar. 19, 2014, 3 pages.
Co-Pending U.S. Appl. No. 13/919,640, Notice of Allowance dated Mar. 17, 2014, 6 pages.
Co-Pending U.S. Appl. No. 13/919,640, Response to Notice of Allowance with RCE dated Feb. 21, 2014, 5 pages.
Co-Pending U.S. Appl. No. 13/919,640, Supplemental Notice of Allowance dated Apr. 10, 2014, 5 pages.
Co-Pending U.S. Appl. No. 12/432,295, Final Rejection dated Jun. 16, 2014, 14 pages.
Co-Pending U.S. Appl. No. 12/432,295, Response to Jun. 16, 2014 Final Rejection filed Oct. 16, 2014, 13 pages.
Co-Pending U.S. Appl. No. 12/906,923, Non-Final Office Action dated Oct. 24, 2014, 11 pages.
Co-Pending U.S. Appl. No. 14/558,631, filed Dec. 2, 2014.

* cited by examiner

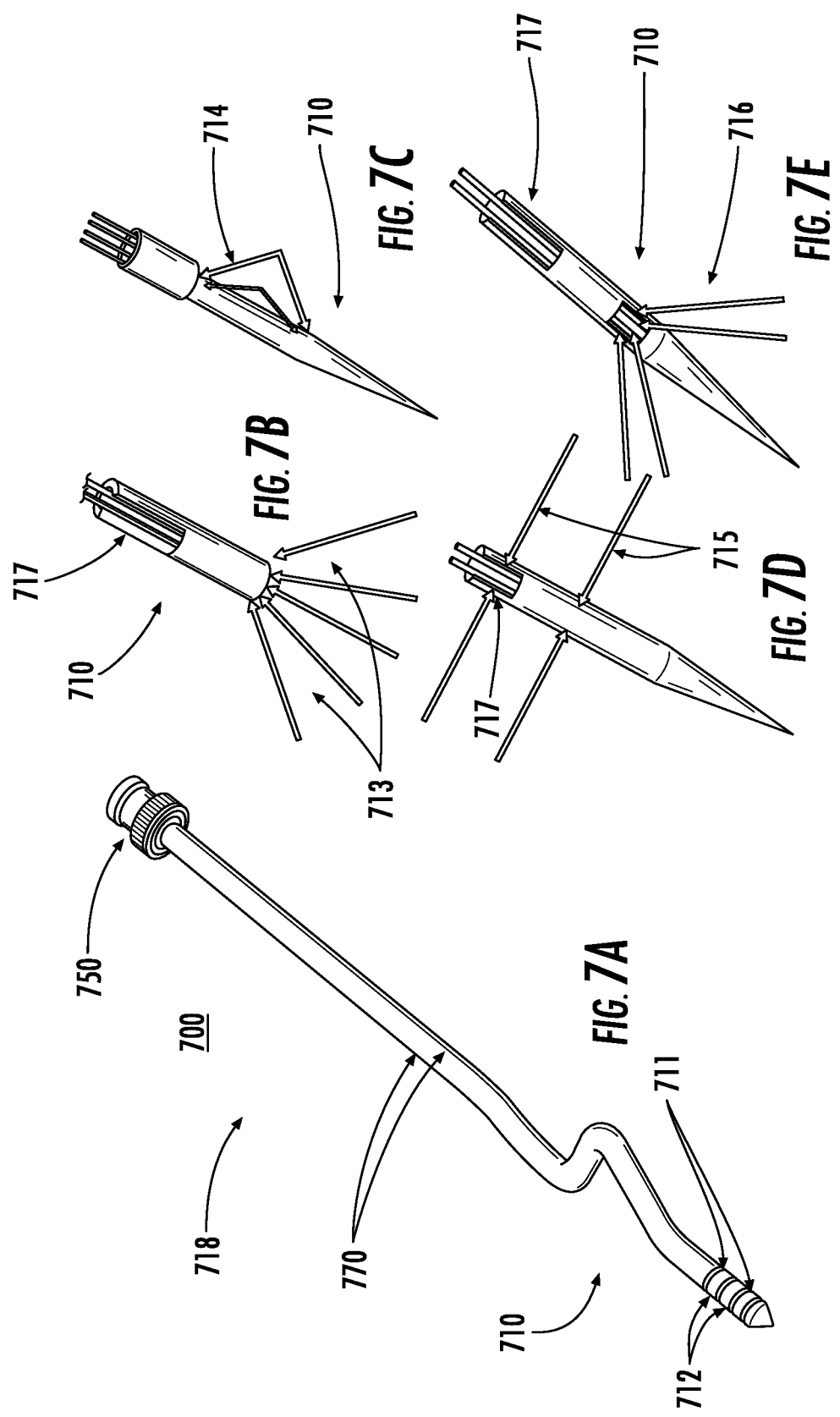

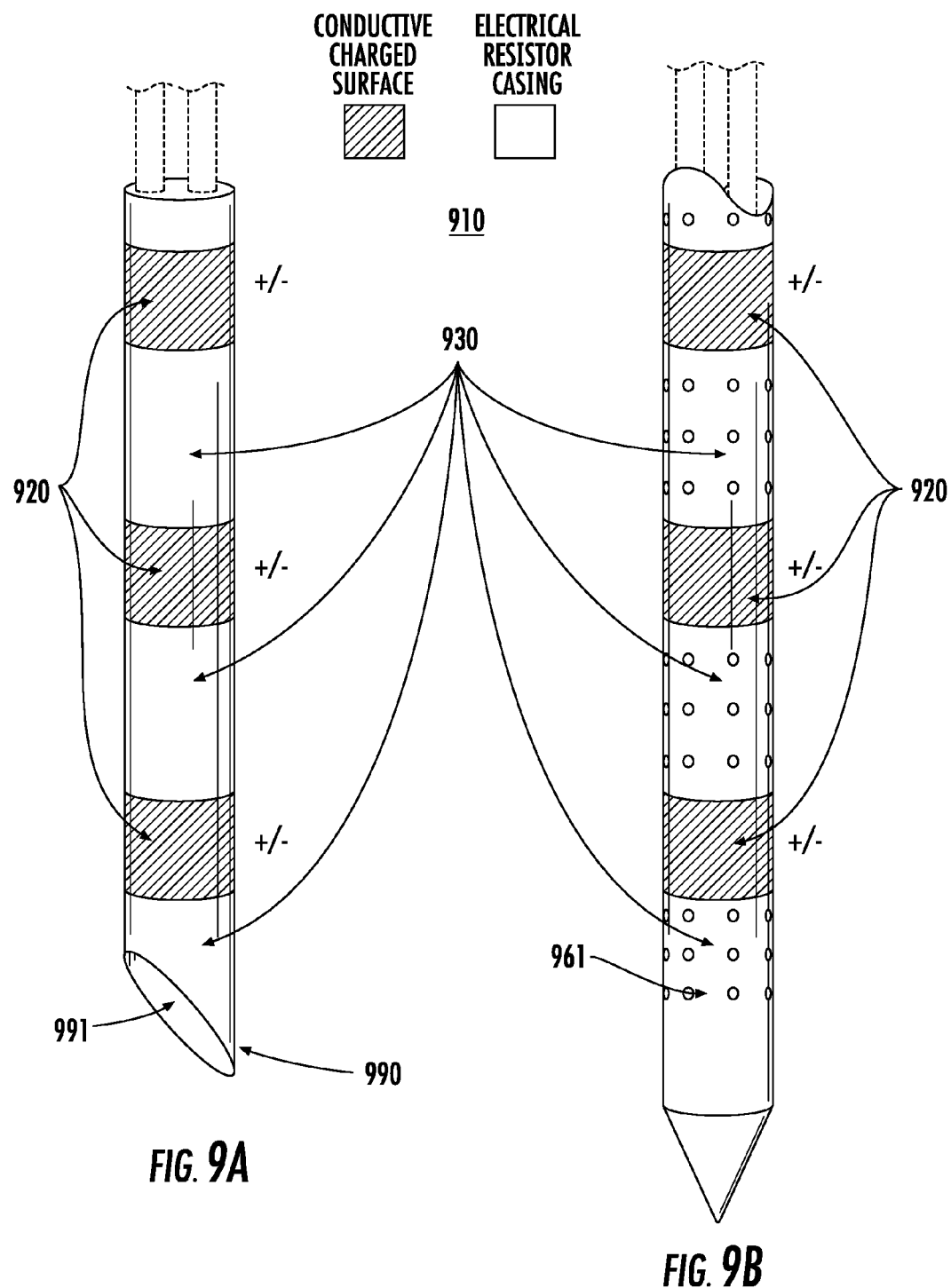

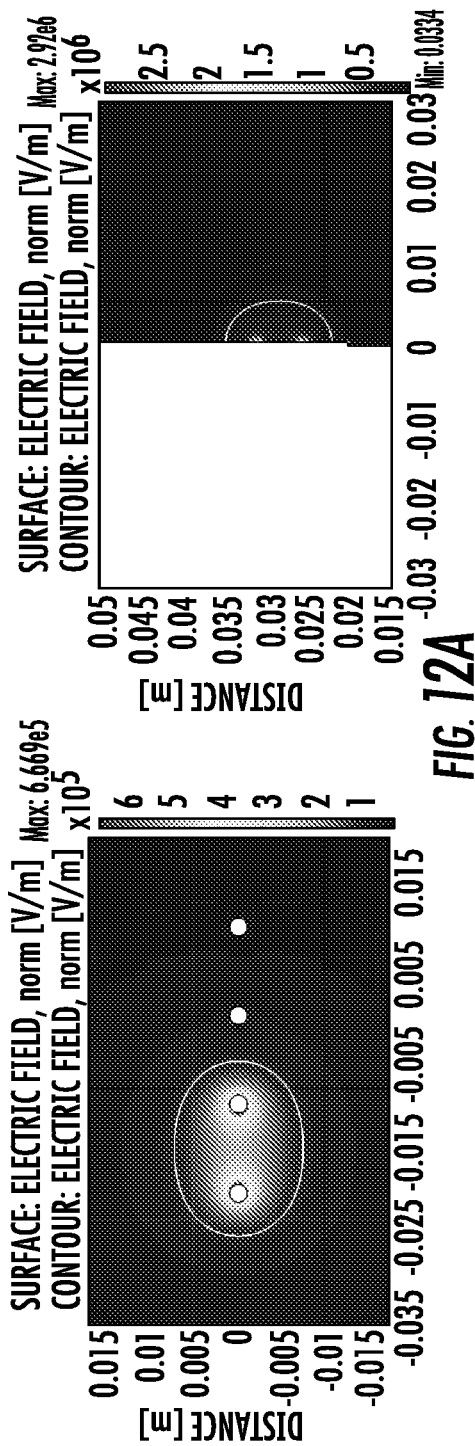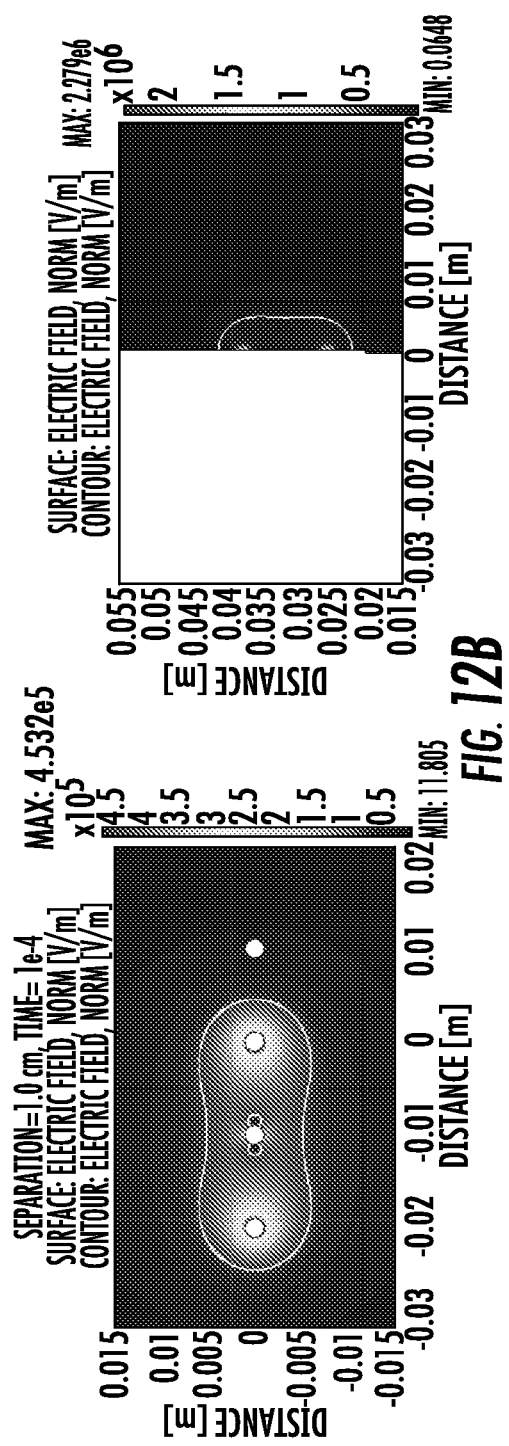
FIG. 12A
FIG. 12B

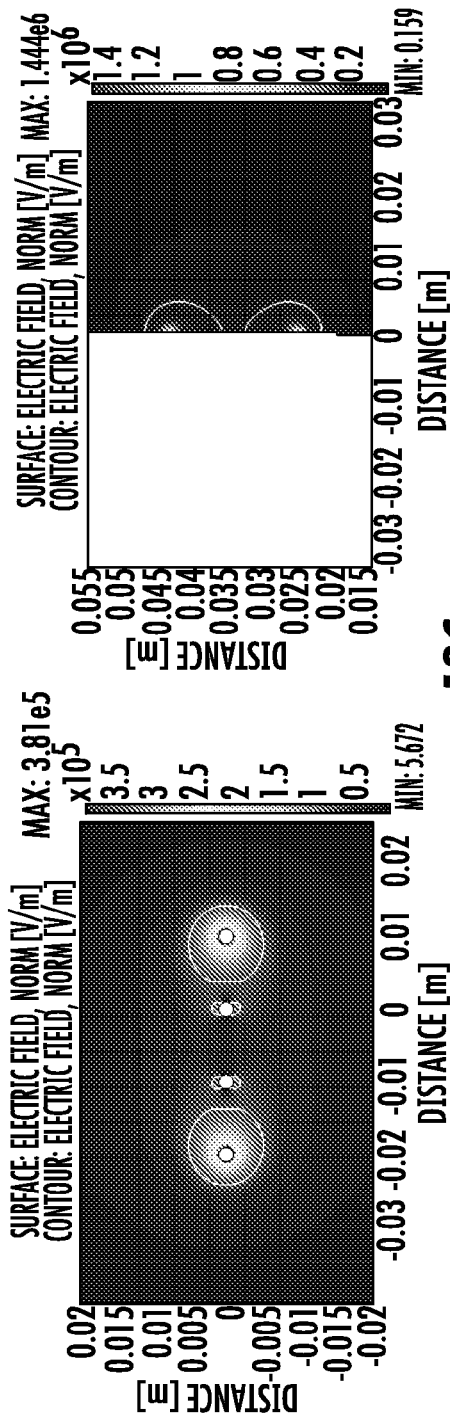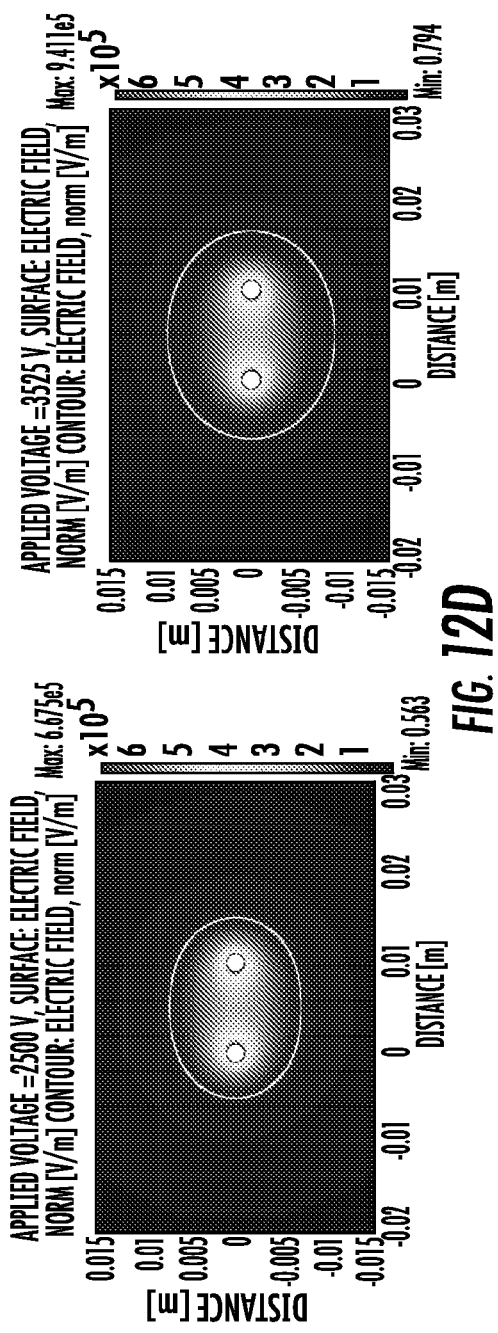
FIG. 12C
FIG. 12D

IRREVERSIBLE ELECTROPORATION TO TREAT ABERRANT CELL MASSES

CROSS-REFERENCE TO RELATED APPLICATIONS

The present application is a Continuation-In-Part application of U.S. patent application Ser. No. 12/432,295, filed on 29 Apr. 2009, which relies on and claims the benefit of the filing date of U.S. provisional patent application No. 61/125,840, filed 29 Apr. 2008. This application also relies on and claims the benefit of the filing dates of U.S. provisional patent application No. 61/171,564, filed 22 Apr. 2009, U.S. provisional patent application No. 61/167,997, filed 9 Apr. 2009, and U.S. provisional patent application No. 61/075,216, filed 24 Jun. 2008. The entire disclosures of all of these patent applications are hereby incorporated herein by reference.

BACKGROUND OF THE INVENTION

1. Field of the Invention

The present invention relates to the field of biomedical engineering and medical treatment of diseases and disorders. More specifically, the invention relates to devices and methods for destroying aberrant cell masses, including tumor tissues, such as cancerous tissues of the brain.

2. Description of Related Art

Treatment of abnormal cell growth in or on normal body tissues and organs can be achieved in many different ways to achieve reduced cell growth, reduction of the resulting aberrant cell mass, and even destruction of the aberrant cell mass. In general, treatments known in the art involve surgical intervention to physically remove the aberrant cell mass, radiation to kill the cells of the aberrant cell mass, exposure of aberrant cells to toxic chemicals (i.e., chemotherapy), or a combination of two or all three of these. While each treatment modality has shown significant effectiveness in treatment of various cell proliferative diseases, no one technique has been shown to be highly effective at treating all types of cell proliferative diseases and disorders. Furthermore, each technique has significant drawbacks. For example, surgical intervention is highly effective at removal of solid tumors on tissues and organs that are physically accessible and capable of sustaining physical damage or capable of regeneration. However, surgical intervention can be difficult to perform on tumors that are not readily accessible or on organs that do not regenerate (e.g., brain tumors), and can involve substantial physical damage to the patient, requiring extensive recuperation times and follow-on treatments. Likewise, treatment with radiation can result in collateral damage to tissue surrounding the tumor, and can cause long-lasting side-effects, which can lower the quality of life of the patient. Similarly, chemotherapeutic treatments cause systemic damage to the patient, and can result in significant side-effects that might require a long recuperation period or permanent damage to the patient.

In the treatment of tumors, including malignant tumors, it is recognized in the medical arts that it is important to achieve ablation of the undesirable tissue in a well-controlled and precise way without affecting the surrounding healthy tissue. The inventors and their colleagues recently developed a new method to treat tumors, known as irreversible electroporation (IRE). The procedure involves placing electrodes within or near the targeted region to deliver a series of low energy, microsecond electric pulses for approximately 1 minute. These pulses permanently destabilize the cell membranes of the targeted tissue (e.g., tumor), thereby killing the cells. IRE does not affect major blood vessels, does not require the use of drugs and non-thermally kills neoplastic cells in a precise and controllable manner, without significantly damaging surrounding tissue. The inventors and their colleagues also recently showed the complete regression in 12 out of 13 treated tumors in vivo using IRE on a type of aggressive sarcoma implanted in nude mice (Al-Sakere, B. et al., 2007, "Tumor ablation with irreversible electroporation." PLoS ONE 2.).

Although advances have been made recently in the field of IRE and the concept of treatment of tumors with IRE has been established, the present inventors have recognized that there still exists a need in the art for improved devices and methods for ablating diseased or disordered tissues, such as tumor tissues, using IRE. The present invention addresses those needs.

SUMMARY OF THE INVENTION

The present invention provides an advancement over tissue ablation techniques previously devised by providing improved devices and methods for precisely and rapidly ablating diseased, damaged, disordered, or otherwise undesirable biological tissues in situ. As used herein, the term ablation is used to indicate destruction of cells, but not necessarily destruction of the underlying extracellular matrix. More specifically, the present invention provides new devices and methods for ablating target tissues for the treatment of diseases and disorders, and particularly tumors of the brain, using IRE. Use of IRE to decellularize diseased tissue provides a controlled, precise way to destroy aberrant cells of a tissue or organ, such as tumor or cancer cells or masses of the brain.

Non-thermal IRE is a method to kill undesirable cells using electric fields in tissue while preserving the ECM, blood vessels, and neural tubes/myelin sheaths. Certain electrical fields, when applied across a cell, have the ability to permeabilize the cell membrane through a process that has come to be called "electroporation". When electrical fields permeabilize the cell membrane temporarily, after which the cells survive, the process is known as "reversible electroporation". Reversible electroporation has become an important tool in biotechnology and medicine. Other electrical fields can cause the cell membrane to become permeabilized, after which the cells die. This deadly process is known as "irreversible electroporation". According to the present invention, non-thermal irreversible electroporation is a minimally invasive surgical technique to ablate undesirable tissue, for example, tumor tissue. The technique is easy to apply, can be monitored and controlled, is not affected by local blood flow, and does not require the use of adjuvant drugs. The minimally invasive procedure involves placing needle-like electrodes into or around the targeted area to deliver a series of short and intense electric pulses that induce structural changes in the cell membranes that promote cell death. The voltages are applied in order to electroporate tissue without inducing significant Joule heating that would significantly damage major blood vessels and the ECM. For a specific tissue type and set of pulse conditions, the primary parameter determining the volume irreversibly electroporated is the electric field distribution within the tissue. Recent IRE animal experiments have verified the many beneficial effects resulting from this special mode of non-thermal cell ablation, such as preservation of major structures including the extracellular matrix, major blood vessels, and myelin sheaths, no scar formation, as well as its promotion of a beneficial immune response. Due to the nature of the function of the brain, in treatment of brain tissues, such as brain tumors, the total electrical charge delivered is at least as important as maintaining low temperature.

In a first aspect, the present invention provides a method for treating aberrant cell growth in animals. In general, the method comprises inserting one or more electrodes into or immediately adjacent to aberrant cell masses and applying IRE to cause irreversible cell death to the aberrant cells. In some embodiments, two or more electrodes are used to treat aberrant cell masses and effect cell death. The electrodes may be present on the same or different devices. Preferably, the parameters for IRE are selected to minimize or avoid excessive heating of the treated tissue and surrounding tissue, thus reducing collateral damage to healthy tissue near the aberrant cell mass. In addition, it is preferable to minimize the total electrical charge delivered when treating brain tissue to avoid complications. The methods are particularly well suited for treatment of aberrant cell growths in or on the brain, as it is important to avoid collateral damage to brain tissue during treatments of that organ. The methods also can be applied to treat a number of other of cancers, including liver cancer, prostate cancer, and pancreatic adenocarcinoma.

Viewed differently, the method for treating aberrant cell growth in animals can be considered a method of treating an animal (including humans) having an aberrant cell growth or mass in or on a tissue or an organ. In exemplary embodiments, the organ is a brain, and the aberrant cell mass is a benign or malignant tumor. Under this view, the method can be a method of treating an animal suffering from a disease or disorder resulting from aberrant cell growth by reducing or eliminating some or all of a mass (e.g., tumor) produced by the aberrant cell growth.

To effect the methods according to the invention, the present invention provides devices designed to treat aberrant cell masses using irreversible electroporation (IRE). While IRE devices have been disclosed prior to the priority date of this document, advanced surgical tools for in vivo IRE to treat diseased tissues and organs had not been developed. The present invention, for the first time, provides devices suitable for in vivo IRE treatment of diseases and disorders, particularly those associated with abnormal cell growth in or on a tissue or organ, which allow for minimally invasive treatment of patients suffering from such abnormal cell growth. The present inventors have designed microsurgical tools to treat currently inoperable tumors in humans and other animals through IRE, and in particular brain tumors. While not so limited, the designs provided herein are sufficient to ablate the majority of tumors smaller than about 3 cm in diameter, such as those about 14 cc in volume or less.

BRIEF DESCRIPTION OF THE DRAWINGS

The accompanying drawings, which are incorporated in and constitute a part of this specification, illustrate several embodiments of the invention, and together with the written description, serve to explain certain principles of the invention.

FIG. 1A shows an MRI before IRE, T2 weighted; FIG. 1B shows superficial non-thermal IRE decellularization site, T2 weighted; and FIG. 1C shows post-contrast T1 weighted; the dog's right is conventionally projected on the left.

FIG. 3A shows a sharp delineation of brain tissue showing the regions of normal and necrotic canine brain tissue after IRE. FIG. 3B shows IRE treated brain tissue showing sparing of major blood vessels.

FIGS. 7A-E are schematic drawings showing various exemplary embodiments of a device according to the invention. Panel A depicts a device, showing a connector, wiring, and electrodes disposed at the tip. Panels B-E depict alternative placement of electrodes, which can be retractable.

FIGS. 9A-B are schematic drawings showing an embodiment of an assembled electrode tip for an exemplary treatment where the tip is inserted within a tumor embedded within benign tissue. Panels A and B depict an embodiment of the device of the invention, comprising a hollow core for delivery of bioactive agents.

FIGS. 12A-E are electrical field outputs from various configurations employing two electrodes. Panel A depicts the use of two electrodes spaced 0.5 cm apart. Panel B depicts the use of two electrodes spaced 1.0 cm apart. Panel C depicts the use of two electrodes spaced 1.5 cm apart. Panel D depicts the use of two electrodes spaced 1.0 cm apart. Panel E depicts a side view of electrical field outputs from one device having two electrically conductive regions separated by an insulative region of a length of 0.5 cm.

DETAILED DESCRIPTION OF VARIOUS EMBODIMENTS OF THE INVENTION

Figure 1A:
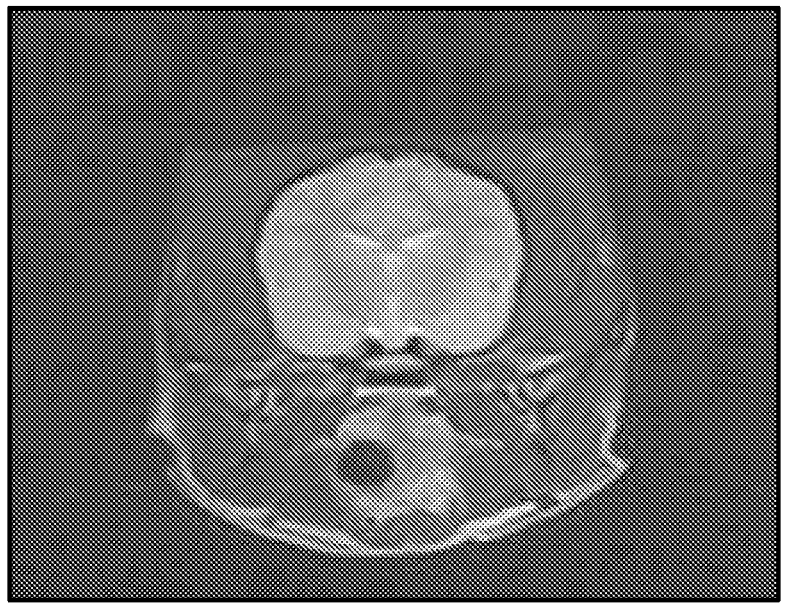
FIGS. 1A-C are magnetic resonance imaging (MRI) images of tissue after non-thermal IRE on canine tissue. The images show that non-thermal IRE decellularization zones were sharply demarcated T1 iso- to hypo-intense, T2 hyper-intense and mild and peripherally contrast enhancing following intravenous administration of gadolinium, consistent with fluid accumulation within decellularization sites and a focal disruption of the blood-brain-barrier.

Reference will now be made in detail to various exemplary embodiments of the invention. It is to be understood that the following discussion of exemplary embodiments is not intended as a limitation on the invention, as broadly disclosed above. Rather, the following discussion is provided to give the reader a more detailed understanding of certain aspects and features of the invention.

Before embodiments of the present invention are described in detail, it is to be understood that the terminology used herein is for the purpose of describing particular embodiments only, and is not intended to be limiting. Further, where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which the term belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the singular forms "a", "an", and "the" include plural referents unless the context clearly dictates otherwise. Thus, for example, reference to "a pulse" includes a plurality of such pulses and reference to "the sample" includes reference to one or more samples and equivalents thereof known to those skilled in the art, and so forth. Furthermore, the use of terms that can be described using equivalent terms include the use of those equivalent terms. Thus, for example, the use of the term "patient" is to be understood to include the terms "subject", "animal", "human", and other terms used in the art to indicate one who is subject to a medical treatment.

Electroporation is the phenomenon in which permeability of the cell membrane to ions and macromolecules is increased by exposing the cell to short (microsecond to millisecond) high voltage electric pulses. The application of the electric pulses can have no effect, can have a transient effect known as reversible electroporation, or can cause permanent permeation known as irreversible electroporation (IRE), which leads to non-thermal cell death by necrosis.

Davalos, Mir, and Rubinsky (Davalos, R. V. et al., 2005, "Tissue ablation with irreversible electroporation." Annals of Biomedical Engineering, 3(2):223-231) recently postulated and demonstrated that IRE can be used as an independent drug-free tissue ablation modality for particular use in cancer therapy. This minimally invasive procedure involves placing electrodes into or around the targeted area to deliver a series of short and intense electric pulses to induce the irreversible structural changes in the membranes. To achieve IRE, the electric field in the targeted region needs to be above a critical value, which is dependent on a variety of conditions such as tissue type and pulse parameters.

The present invention extends and improves on prior techniques for IRE by providing new methods and devices for IRE treatment of solid tumors, including those associated with brain cancer. Because the brain is susceptible to small fluctuations in temperature, the present invention provides devices and techniques for non-thermal IRE to kill undesirable cells and tissues. In addition, because the brain functions by way of electrical charges, the present invention provides devices and techniques that limit or precisely control the amount of electrical charge delivered to tissue. To achieve the invention, a device has been developed that contains both conducting and non-conducting surfaces and that is capable of delivering controlled pulses of electricity to tumor tissues while substantially protecting surrounding healthy tissue. In exemplary embodiments, the device has a laminate structure of at least one electrically conductive and at least one electrically insulative material. In some exemplary embodiments, the device has at least two concentric disk electrodes separated by an insulating material similar in dimensions to those already used in deep brain stimulation (DBS). DBS is an FDA approved therapy that alleviates the symptoms of otherwise treatment-resistant disorders, such as chronic pain, Parkinson's disease, tremor, and dystonia. The Examples, below, present results demonstrating that an IRE procedure does not induce substantial thermal effects in the brain, and delivers electrical charges to highly defined regions of tissues, supporting the conclusion that IRE can be used as a minimally invasive surgical technique for the treatment of brain cancer and other diseases and disorders involving aberrant cell mass development. The methods employ the unique designs discussed herein, which provide improved controlled delivery of electrical pulses with controlled three-dimensional patterns and controlled thermal outputs. The present devices and systems provide surgical tools and methods for IRE treatment of subcutaneous tumors that expand the application space for this new technology, with the potential to treat a number of cancers, including brain, liver, prostate and pancreatic adenocarcinoma.

The following detailed description focuses on devices, systems, and methods for treatment of brain cancer. However, those of skill in the art will recognize that the concepts discussed have equivalent application to other diseases and disorders involving aberrant cell growth and/or production of deleterious cell masses on organs and tissues.

While the prognosis for many patients has improved with new drugs and radiosurgery, options to treat primary brain tumor patients are limited because of the need for techniques to be non-thermal, i.e., not propagate a convective hot spot in normal brain tissue not being treated. The current invention allows for IRE as an extremely useful, minimally invasive surgical technique for the treatment of brain cancer. The present designs for a surgical tool/treatment system for brain cancer is readily translated into the development of tools for other types of cancer.

As mentioned above, the present invention provides a method for treating aberrant cell growth in animals. The aberrant cell growth can be any type of aberrant cell growth, but in exemplary embodiments detailed herein, it is generally described in terms of tumors, such as brain tumors. In general, the method of treating comprises temporarily implanting one or more electrodes, which may be present on the same or different devices, into or immediately adjacent a tumor, and applying an electrical field to the tumor in multiple pulses or bursts over a prescribed or predetermined period of time to cause irreversible cell death to some or all of the tumor cells. Preferably, irreversible damage to non-tumor cells in proximity to the tumor is minimal and does not result in significant or long-lasting damage to healthy tissues or organs (or a significant number of cells of those tissues or organs). According to the method of the invention, cell killing is predominantly, essentially, or completely due to non-thermal effects of the electrical pulsing. The method further comprises removing the electrode(s) after suitable treatment with the electrical fields. As a general matter, because the method involves temporary implantation of relatively small electrodes, it is minimally invasive and does not result in the need for significant post-treatment procedures or care. Likewise, it does not result in significant ancillary or collateral damage to the subject being treated.

In practicing the method, the number of electrodes, either on a single or multiple devices, used can be selected by the practitioner based on the size and shape of the tumor to be treated and the size and shape of the electrode. Thus, embodiments of the invention include the use of one, two, three, four, five, or more electrodes. Each electrode can be independently sized, shaped, and positioned in or adjacent the tumor to be treated. In addition, the number and spacing of electrodes on a single device can be adjusted as desired. As detailed below, the location, shape, and size of electrodes can be selected to produce three-dimensional killing zones of numerous shapes and sizes, allowing for non-thermal treatment of tumors of varying shapes and sizes.

Surprisingly, it has been found that pulse durations for ablation of solid tumors can be relatively short, thus reducing the probability of generation of thermal conditions and excessive charges that cause collateral damage to healthy tissues. More specifically, the present invention recognizes for the first time that, in contrast to prior disclosures relating to IRE, the pulse length for highly efficient tissue ablation can be lower than 100 microseconds (100 us). Indeed, it has surprisingly been determined that a pulse length of 25 us or lower can successfully cause non-thermal cell death. Thus, in embodiments, the method of treatment uses pulse lengths of 10 us, 15 us, 20 us, 25 us, 30 us, 35 us, 40 us, 45 us, 50 us, 55 us, 60 us, 65 us, 70 us, 75 us, 80 us, 85 us, or 90 us. Preferably, to most effectively minimize peripheral damage due to heat, pulse lengths are limited to 90 us or less, for example 50 us or less, such as 25 us. By reducing the pulse length, as compared to prior art techniques for IRE, larger electric fields can be applied to the treatment area while avoiding thermal damage to non-target tissue (as well as to target tissue). As a result of the decreased pulse length and concomitant reduction in heat production, the methods of the invention allow for treatment of tissues having higher volumes (e.g., larger tumors) than possible if prior art methods were to be employed for in vivo treatment of tumors.

It has also been determined that voltages traditionally used for IRE are too high for beneficial treatment of tumors in situ. For example, typically, IRE is performed using voltages of between 4000 V/cm to 1500 V/cm. The present invention provides for use of voltages of much lower power. For example, the present methods can be performed using less than 1500 V/cm. Experiments performed by the inventors have shown that 2000 V/cm can cause excessive edema and stroke in patients when applied to brain tissue. Advantageously, for treatment of brain tumors, applied fields of about 500 V/cm to 1000 V/cm are used. Thus, in general for treatment of brain tumors, applied fields of less than 1000 V/cm can be used.

Further, it has been discovered that the number of electrical pulses that can be applied to successfully treat tumors can be quite high. Prior art methods of using IRE for various purposes included the use of relatively few pulses, for example 8 pulses or so. Reports of use of up to 80 pulses for IRE have been published; however, to the inventors' knowledge, a higher number of pulses has not been recommended. The present invention provides for the use of a relatively high number of pulses, on the order of 90 pulses or greater. For example, in exemplary embodiments, 90 pulses are used. Other embodiments include the use of more than 90 pulses, such as 100 pulses, 110 pulses, or more.

According to the method of the invention, cycle times for pulses are set generally about 1 Hz. Furthermore, it has been found that alternating polarity of adjacent electrodes minimizes charge build up and provides a more uniform treatment zone. More specifically, in experiments performed by the inventors, a superficial focal ablative IRE lesion was created in the cranial aspect of the temporal lobe (ectosylvian gyrus) using the NanoKnifeB (Angiodynamics, Queensbury, N.Y.) generator, blunt tip bipolar electrode (Angiodynamics, No. 204002XX) by delivering 9 sets of ten 50 us pulses (voltage-to-distance ratio 2000 V/cm) with alternating polarity between the sets to prevent charge build-up on the stainless steel electrode surfaces. These parameters were determined from ex-vivo experiments on canine brain and they ensured that the charge delivered during the procedure was lower than the charge delivered to the human brain during electroconvulsive therapy (an FDA approved treatment for major depression). Excessive charge delivery to the brain can induce memory loss, and thus is preferably avoided.

The method of the invention encompasses the use of multiple electrodes and different voltages applied for each electrode to precisely control the three-dimensional shape of the electric field for tissue ablation. More specifically, it has been found that varying the amount of electrical energy emitted by different electrodes placed in a tissue to be treated allows the practitioner to finely tune the three-dimensional shape of the electrical field that irreversibly disrupts cell membranes, causing cell death. Likewise, the polarity of electrodes can be varied to achieve different three-dimensional electrical fields. Furthermore, one of the advantages of embodiments of the invention is to generate electric field distributions that match complex tumor shapes by manipulating the potentials of multiple electrodes. In these embodiments, multiple electrodes are energized with different potential combinations, as opposed to an "on/off" system like radio frequency ablation, to maximize tumor treatment and minimize damage to surrounding healthy tissue.

According to the method of the invention, the separation of the electrodes within or about the tissue to be treated can be varied to provide a desired result. For example, the distance between two or more electrodes can be varied to achieve different three-dimensional electrical fields for irreversible disruption of cell membranes. The three-dimensional shape can thus be set to ablate diseased tissue, but partially or completely avoid healthy tissue in situations where the interface between healthy and diseased tissue shows a complex three dimensional shape.

The methods of the invention are well suited for treatment of tumors using non-thermal IRE. To better ensure that cell ablation is a result of non-thermal effect, and to better protect healthy tissue surrounding the site of treatment, the method can further comprise cooling the electrodes during the treatment process. By applying a heat sink, such as a cooling element in an electrode (discussed below), generation of heat in and around tissue in close proximity to the electrodes can be minimized, resulting in a more consistent application of non-thermal IRE to the tissue and a more controlled application of cell killing to only those tissues desired to be treated.

The method of the invention, in embodiments, includes the use of electrodes of different sizes and shapes. Studies performed by the inventors have shown that the electrical field distribution may be altered by use of electrodes having different diameters, lengths, and shapes. Thus, the use of different sizes and shapes of conducting surfaces can be used to control the electrical fields used for cell ablation. In certain embodiments, the method includes the use of a variable size electrode. For example, an electrode may be used that, in one configuration has a relatively small diameter, which is used for minimally invasive implantation of the electrode into the site to be treated. Once inserted, a sheath or other covering can be retracted to allow expansion of the electrode tip to a different size for application of the electric field. After treatment, the sheath can be moved to cover the tip again, thus reducing the size of the tip to its original size, and the electrode withdrawn from the treated tissue. The expandable element can be thought of as a balloon structure, which can have varying diameters and shapes, depending on original material shape and size.

The methods of the invention comprise, in embodiments, treatment of tissue surrounding tumor tissue. The surrounding tissue is treated by way of reversible electroporation. As such, bioactive agents can be introduced into the reversibly electroporated cells. In such embodiments, additional cell killing, under controlled conditions, can be effected in healthy tissue. Such a treatment is preferred when treating highly aggressive malignant tumors, which often show invasion of healthy tissue surrounding the tumor. Alternatively, the bioactive agents can provide a protective effect to cells in which they are introduced via reversible electroporation.

In embodiments, the method for treating aberrant cell growth in animals is a method of treating a subject suffering from a tumor. It thus may be a method of treating a subject suffering from cancer. Using different terminology, the method can be a method of treating a tumor or a method of treating cancer. As such, the method can be a method of treating either a benign tumor or a malignant tumor. In embodiments, the method is best suited for treatment of solid tumors. In exemplary embodiments, the method is a method of treating a subject suffering from a brain tumor, such as brain cancer.

In clinical settings, the method of treating according to the invention can have ameliorative effects or curative effects. That is, a method of treating a subject can provide a reduction in cell growth of a tumor, a reduction in tumor size, or total ablation of the tumor.

The method of the invention can include a single round of treatment or two or more rounds of treatment. That is, the method of cell ablation, either intentionally or as a result of tumor size or shape, can result in less than complete destruction of a tumor. In such a situation, the method can be repeated one or more times to effect the desired level of tumor reduction. As the method of the invention is relatively minimally invasive, multiple rounds of treatment are not as harmful to the patient than multiple rounds of traditional surgical intervention.

The method of the invention can be part of a multi-modal treatment. The method thus may comprise other cell-killing techniques known in the art. For example, the method may further comprise exposing the tumor to radiation, or treating the patient with a chemotherapeutic agent. It likewise may be performed after or between surgical intervention to remove all or part of a tumor. Those of skill in the art are fully aware of the parameters for treatment with other modalities; thus, details of those treatment regimens need not be detailed herein.

The method of the invention is implemented using devices and systems. The devices according to the invention are suitable for minimally invasive temporary implantation into a patient, emission of a tissue-ablating level of electricity, and removal from the patient. The device according to the invention thus may be used in the treatment of tumors and the treatment of patients suffering from tumors. The devices can take multiple forms, based on the desired three-dimensional shape of the electrical field for cell killing. However, in general, the devices include two or more regions of differing conductivity. In some embodiments, the device comprises alternating regions of conductivity, for example a region of electrical conductivity, which is adjacent a region of electrical non-conductivity, which is adjacent a different region of conductivity. In embodiments, the device comprises two or more layers of conductive and insulative materials, in a laminate structure with alternating conductive properties. To protect tissue that is not to be treated, the outer layer can be insulative except at the region where treatment is to be effected. According to embodiments of the device, the amount of conductive material exposed to the tissue to be treated can be adjusted by a movable non-conductive element disposed on the outer surface of the device.

Further, in general, the device takes a rod-like shape, with one dimension (i.e., length) being substantially longer than the other (i.e., width or diameter). While exemplary embodiments are configured in a generally cylindrical shape, it is to be understood that the cross-sectional shape of the electrode can take any suitable geometric shape. It thus may be circular, square, rectangular, oval, elliptical, triangular, pentagonal, hexagonal, octagonal, etc.

The devices of the invention comprise one or more electrodes, which are electrically conductive portions of the device. The devices are thus electrically conductive elements suitable for temporary implantation into living tissue that are capable of delivering an electrical pulse to the living tissue. The device of the invention has a proximal end and a distal end. The proximal end is defined as the end at which the device is attached to one or more other elements, for control of the function of the device. The distal end is defined by the end that contacts target tissue and delivers electrical pulses to the tissue. The distal end thus comprises an exposed or exposable electrically conductive material for implantation into a target tissue. Typically, the distal end is described as including a "tip" to denote the region of the distal end from which an electrical pulse is delivered to a tissue. The device further comprises at least one surface defining the length and circumference of the device.

In exemplary embodiments, the device comprises a laminate structure, with alternating conductive and non-conductive or insulative layers expanding outward from the proximal-distal center axis to the surface of the device. In typical embodiments, the center most layer, which shows the smallest diameter or width, is electrically conductive and comprises a part of the electrode tip. However, in alternative embodiments, the center-most layer is an open channel through which a fluid may be passed or through which additional physical elements may be placed. Yet again, the center-most layer may comprise an insulative material. In embodiments comprising a laminate structure, the structure can provide a more customizable electric field distribution by varying the separation distances between electrically conductive regions. Alternatively, in embodiments, certain electrically conductive regions can be exposed or concealed by movement of an outer, non-conductive sheath. In embodiments that do not comprise a laminate structure, the separation lengths can be achieved by disposing on the surface non-conductive materials at various regions.

In some embodiments, one or more substantially open channels are disposed along the center axis or in place of one of the conductive or insulative layers. The channel(s) may be used as heat sinks for heat produced by the device during use. In embodiments, water or another fluid is held or entrained in the channel to absorb and/or remove heat.

The device of the invention comprises an electrode tip at the distal end. The electrode tip functions to deliver electrical pulses to target tissue. The tip may be represented by a single conductive layer of the device or may be represented by two or more conductive layers that are exposed to the tissue to be treated. Furthermore, the tip may be designed to have any number of geometrical shapes. Exemplary embodiments include tips having a needle-like shape (i.e., electrical pulses emanate from a small cone-like structure at the distal end of the device) or having a circular shape (i.e., electrical pulses emanate from the cylindrical outer surface of the device, which is a section of the device where the outer insulative layer has been removed to expose the next layer, which is conductive). For use in treatment of brain tumors, the tip advantageously comprises a blunt or rounded end to minimize laceration of brain tissue. In embodiments, the rounded or blunt end comprises a hole that allows for a sharp or needle-like structure to be deployed into tumor tissue at the appropriate time.

The device comprises a proximal end, which generally functions for attachment of the device to a power source/controller and a handle. The proximal end thus may comprise connections for electrical wires that run from the power source/controller to the electrically conductive layers of the device. Standard electrical connections may be used to connect the conductive elements to the wires. In embodiments, the device is attached to a handle for ease of use by a human. While not limited in the means for attaching the device to the handle, in embodiments, the connection is made by way of a friction fit between the outer surface of the device and the handle, for example by way of an insulative O-ring (e.g., a Norprene O-ring) on the handle. In other embodiments, the device comprises, on its outer surface, ridges or other surface features that mate with surface features present on the handle. In yet other embodiments, the proximal end comprises one or more structures that allow for controlled movement of the outer surface along the length of the device. In such embodiments, the outer surface will comprise an outer sheath that is electrically non-conductive, and which surrounds an electrically conductive layer. Using the structures at the proximal end, the outer sheath may be moved, relative to the rest of the device, to expose or conceal varying portions of the electrically conductive material beneath it. In this way, the amount of surface area of the conductive material at the tip can be adjusted to provide a desired height of exposure of tissue to the electrode tip. Of course, other structures for securely fastening the device to a holder may be used, such as clips, set screws, pins, and the like. The device is not limited by the type of structure used to connect the device to the holder.

The device of the invention can be designed to have any desired size. Typically, it is designed to be minimally invasive yet at the same time suitable for delivery of an effective electrical field for IRE. The diameter or width is thus on the order of 0.5 mm to 1 cm. Preferably, the diameter or width is about 0.5 mm to about 5 mm, such as about 1 mm, 2 mm, 3 mm, or 4 mm. The length of the device is not particularly limited, but is generally set such that a surgeon can use the device comfortably to treat tumors at any position in the body. Thus, for human use, the device is typically on the order of 40 cm or less in length, such as about 30 cm, 25 cm, or 15 cm, whereas for veterinary use, the length can be much larger, depending on the size of animal to be treated. For treatment of human brain tumors, the length can be on the order of 40 cm.

In some embodiments, the device, or a portion of it, is flexible. A flexible device is advantageous for use in accessing tumors non-invasively or minimally invasively through natural body cavities. In embodiments where the device or a portion of it is flexible, the shape of the device can change based on contact with body tissues, can be pre-set, or can be altered in real-time through use of wires or other control elements, as known in the art, for example in use with laparoscopic instruments.

The device of the invention can be part of a system. In addition to the device, the system can comprise a handle into or onto which the device is disposed. The handle can take any of a number of shapes, but is generally designed to allow a surgeon to use the device of the invention to treat a patient in need. It thus typically has a connector for connecting the device to the holder, and a structure for the surgeon to grasp and maneuver the device. The handle further can comprise a trigger or other mechanism that allows the surgeon to control delivery of electrical pulses to the device, and thus to the tissue to be treated. The trigger can be a simple on/off switch or can comprise a variable control that allows for control of the amount of power to be delivered to the device. Additionally, the handle may be created in such a manner that it may be attached to additional pieces of equipment, such as ones that allow precise placement of the electrode relative to an inertial or the patient's frame of reference, allowing steady and accurate electrode positioning throughout an entire procedure, which may entail the application of electric pulses in addition to radiotherapy, imaging, and injections (systemically and locally) of bioactive agents. Furthermore, the handle may be attached to machines that are operated remotely by practitioners (e.g., the Da Vinci machine).

The system can further comprise a power source and/or a power control unit. In embodiments, the power source and control unit are the same object. The power source provides electrical power to the device, typically by way of an electrical connection through the handle. The power source can be any suitable source that can deliver the proper amount of electrical power to the device of the invention. Suitable power sources are commercially available, and the invention is not limited by the type or manufacturer. The power control unit provides the user with the ability to set the power output and pulse time for electrical pulses to be delivered to the device, and thus to the tissue to be treated. Suitable control units are commercially available, and the invention is not limited by the type or manufacturer. For example, an appropriate power source/controller is available from Angiodynamics (Queensbury, N.Y.).

The device of the invention can be disposable or reusable. Where the device is designed to be reusable, it is preferably fabricated from materials that can be sterilized multiple times without destruction of the device. For example, the device can be fabricated from rust-resistant metals or alloys, such as stainless steel, and plastic or other synthetic polymeric materials that can withstand cleaning and sterilization. Exemplary materials are those that can be subjected to detergents, steam heat (e.g., autoclaving), and/or irradiation for at least one cycle of sterilization. Those of skill in the art can select the appropriate materials without undue experimentation, based on materials used in other medical devices designed to withstand common sterilization techniques.

EXAMPLES

The invention will be further explained by the following Examples, which are intended to be purely exemplary of the invention, and should not be considered as limiting the invention in any way.

As a general background to the Examples, it is noted that the inventors and their colleagues have successfully demonstrated decellularization using IRE 1) in vivo and ex vivo, 2) to show that different tissues can be utilized, 3) to show that the area affected can be predicted using numerical modeling, 4) to show how numerical modeling can be used to ensure the ECM, blood vessels, and neural tubes are not thermally damaged, 5) while the organ was attached to a perfusion system, 6) while demonstrating preservation of major vasculature and ECM, and 7) with verification through imaging.

Example 1

IRE Performance Indicia

To illustrate 1) the possibility to monitor creation of a cell-free tissue section in brain in real-time using imaging techniques, 2) the variety of tissues that can be used, and 3) how to preserve vasculature, a healthy female purpose bred beagle was used. Nine sets of ten pulses were delivered with alternating polarity between the sets to minimize charge build-up on the electrode surfaces. The maximum voltage-to-distance ratio used was 2000 V/cm because the resulting current did not exceed 2 amps. The charge that was delivered to the brain during the IRE procedure was 22.5 mC, assuming ninety pulses (50 µs pulse durations) that would result from a maximum hypothetical current of 5 amps.

TABLE 1

| | IRE pulse parameters | | | | | |
|---|---|---|---|---|---|---|
| ELECTRODES | EXPOSURE LENGTH [mm] | GAP DISTANCE [mm] | VOLTAGE [V] | VOLTAGE TO DISTANCE RATIO [V/cm] | PULSES | PULSE DURATION [µs] |
| 1 mm Monopolar | 5 | 5 | 500 | 1000 | 90 | 50 |
| Bipolar | Standard | 7 | 1600 | 2000 | 90 | 50 |

Method: After induction of general anesthesia, a routine parietotemporal craniectomy defect was created to expose the right temporal lobe of the brain. Two decellularization sites were performed: 1) a deep lesion within the caudal aspect of the temporal lobe using a monopolar electrode configuration (6 mm electrode insertion depth perpendicular to the surface of the target gyrus, with 5 mm interelectrode distance), and 2) a superficial lesion in the cranial aspect of the temporal lobe using a bipolar electrode (inserted 2 cm parallel to the rostrocaudal length of the target gyrus, and 2 mm below the external surface of the gyrus). Intraoperative adverse effects that were encountered included gross microhemorrhages around the sharp monopolar electrode needles following insertion into the gyrus. This hemorrhage was controlled with topical application of hemostatic foam. Subject motion was completely obliterated prior to ablating the superficial site by escalating the dose of atracurium to 0.4 mg/kg. Grossly visible brain edema and surface blanching of the gyrus overlying the bipolar electrode decellularization site was apparent within 2 minutes of completion of IRE at this site. This edema resolved completely following intravenous administration of 1.0 g/kg of 20% mannitol. No adverse clinically apparent effects attributable to the IRE procedure, or significant deterioration in neurologic disability or coma scale scores from baseline evaluations were observed. However, the results indicated to the inventors that a lower voltage would provide adequate results but with less ancillary trauma to the brain.

Figure 1B:
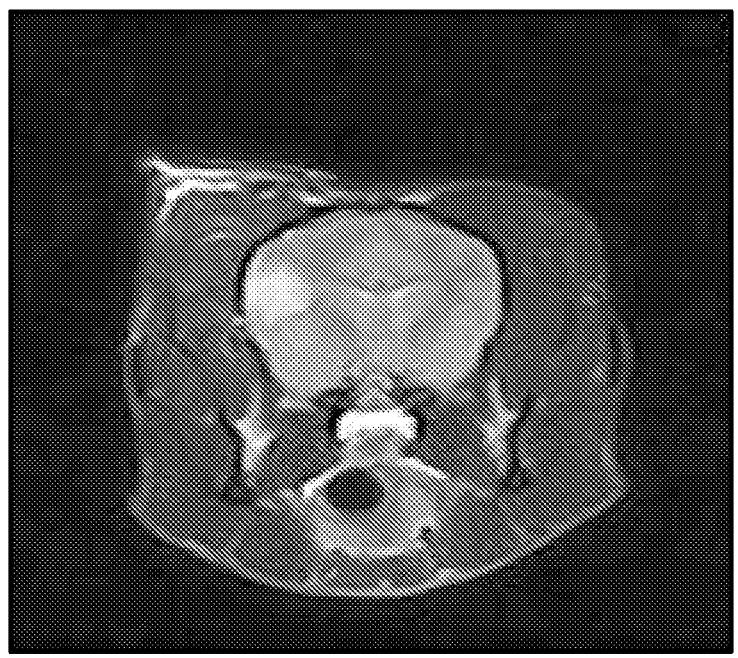
Figure 1C:

Methods to monitor creation of cell-free tissues in vivo: A unique advantage of IRE to ablate tissues in vivo is its ability to be monitored in real-time using imaging techniques, such as electrical impedance tomography, MRI, and ultrasound. Below, this Example shows MRI examinations performed immediate post-operatively, which demonstrate that IRE decellularization zones were sharply demarcated (FIGS. 1A-C).

Figure 2:
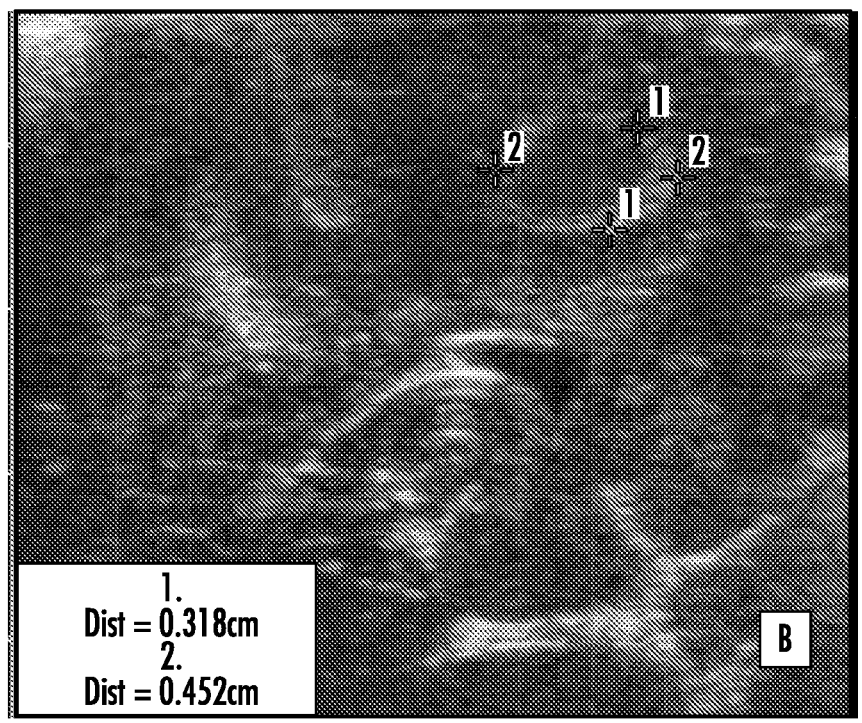
FIG. 2 shows an ultrasound image of brain tissue 24 hour post-IRE treatment. The IRE decellularization zone is clearly visible as a well demarcated, hypoechoic circular lesion with a hyperechoic rim.

As shown in FIG. 1, neurosonography performed intraoperatively and at 1 hour and 24 hours post-procedure demonstrated clearly demarcated decellularization zones and visible needle tracts within the targeted brain parenchyma. Intraoperatively and immediately postoperatively, the decellularization zones appeared as hypoechoic foci with needle tracts appearing as distinct hyperechoic regions (FIG. 2). Neurosonographically, at the 24 hour examination the IRE decellularization zone was hypoechoic with a hyperechoic rim (FIG. 2). Compared to the 1 hour post-operative sonogram, the IRE decellularization zone appeared slightly larger (1-2 mm increase in maximal, two dimensional diameter). EEG performed in the post-operative period revealed focal slowing of the background rhythm over the right temporal region in association with the decellularization zones.

Figure 3:
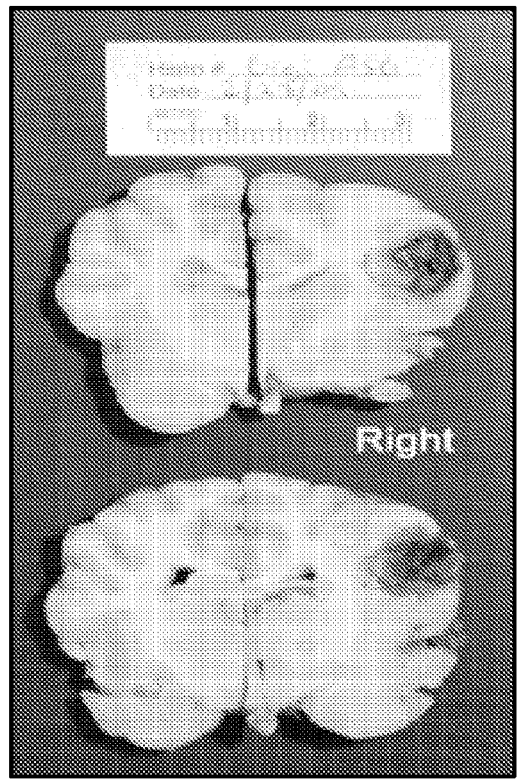
FIG. 3 depicts images of brain tissue after non-thermal IRE treatment.

Macrolevel and histologic verification of treating cells: The brain was collected within 2 hours of the time of death and removed from the cranium. Care was taken to inspect soft tissues and areas of closure created at the time of surgery. The brain was placed in 10% neutral buffered formalin solution for a minimum of 48 hours. Then, the brain was sectioned at 3 mm intervals across the short axis of the brain, in order to preserve symmetry and to compare lesions. Following gross dissection of fixed tissues, photographs were taken of brain sections in order to document the position and character of lesions, as shown in FIG. 3. Readily apparent in gross photographs of the sectioned brain are lesions created either by the physical penetration of brain substance with electrodes or created by the application of pulse through the electrodes. There are relatively well-demarcated zones of hemorrhage and malacia at the sites of pulse delivery.

Figure 4A:
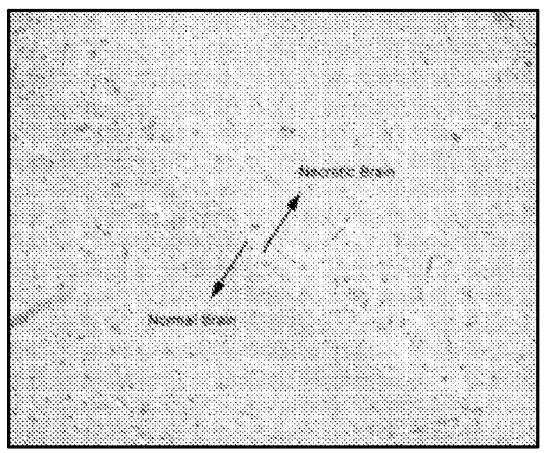
FIGS. 4A-B are photographs of fixed brain sections to show position and character of decellularized volume.
Figure 4B:
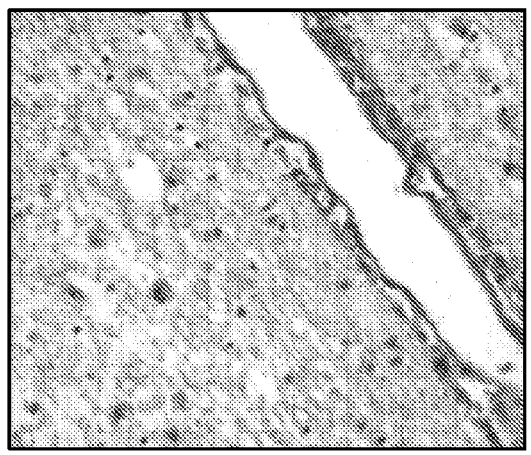

Microscopic lesions correlated well with macroscale appearance. Areas of treatment are represented by foci of malacia and dissociation of white and grey matter. Small perivascular hemorrhages are present and there is sparing of major blood vessels (see FIG. 4B). Notable in multiple sections is a relatively sharp line of demarcation (approximately 20-30 micrometers) between areas of frank malacia and more normal, organized brain substance (see FIG. 4A).

Figure 5:
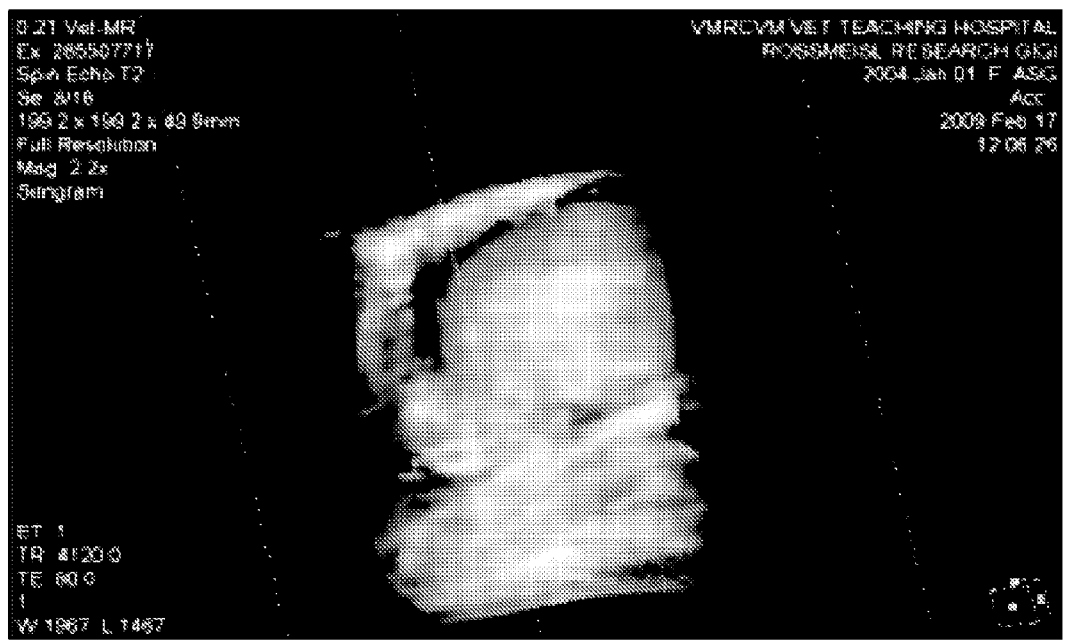
FIG. 5 shows a three-dimensional MRI source reconstruction of a superficial lesion site.

Analysis to determine IRE threshold: To determine the electric field needed to irreversibly electroporate tissue, one can correlate the lesion size that was observed in the ultrasound and MRI images with that in the histopathological analysis to determine the percentage of lesion growth. Decellularized site volumes can be determined after identification and demarcation of IRE decellularization zones from surrounding brain tissue using hand-drawn regions of interest (ROI). A representative source sample image is provided in FIG. 5.

Example 2

Use of IRE to Kill Brain Cells

There are advantages to a strategy to treat cancer using IRE. IRE to treat cancer has advantages over existing thermal ablation, including the ability to: monitor what area has been irreversibly electroporated in real-time using ultra-sound or other imaging techniques; spare neural tubes and blood vessels, enabling treatment in otherwise inoperable areas; preserve the microvasculature, which promotes rapid healing of the treated volume; predict the affected area using numerical modeling for designing protocols; not be affected by blood flow as is the temperature distribution during thermal therapies; image the success of the treatment using MRI or other imaging techniques; and administer the electric fields in time periods of less than 5 minutes.

The present methods and devices provide a technology for treatment of tumors with IRE. Prior to the present invention, devices designed to irreversibly electroporate deep tissues did not exist. The experiments conducted and reported in the prior art utilized reversible electroporation systems. These devices usually consist of large plate electrodes (intended for transdermal drug delivery), needle electrodes with a large probe (intended for targeting in or for small animal studies), or cuvettes (used for in vitro applications). Applying an electric pulse over the skin presents challenges for deep tissue applications due to the significant voltage drop across the skin, generating considerable skin damage. (The same issue arises with an organ containing an epithelial layer.) Other devices that use needle electrodes are limited to superficial tumors. Furthermore, these tools have a large mechanical housing making the treatment of subcutaneous tumors impossible without invasive surgery. A tool designed specifically for IRE for subcutaneous delivery of the electric field dramatically enhances the application space of IRE for tissue ablation.

To provide an initial proof of concept, a device according to the invention was used to kill brain cells in vitro. Representing a unique pathobiological phenomenon, high-grade canine gliomas exhibit essentially the same properties as human gliomas, including pathology (markers), genetics, behavior (invasiveness), lack of metastases, and a similar clinical course of the disease. Dogs diagnosed with these tumors have poor prognosis and most are humanely euthanized to prevent further suffering from the progression of the disease. Primary brain tumors (PBTs) account for 1-3% of all deaths in aged dogs where necropsy is performed. The many similarities of glial tumors in people and dogs make these tumors in dogs an excellent translational approach for new diagnostic and treatment methods.

Figure 6:
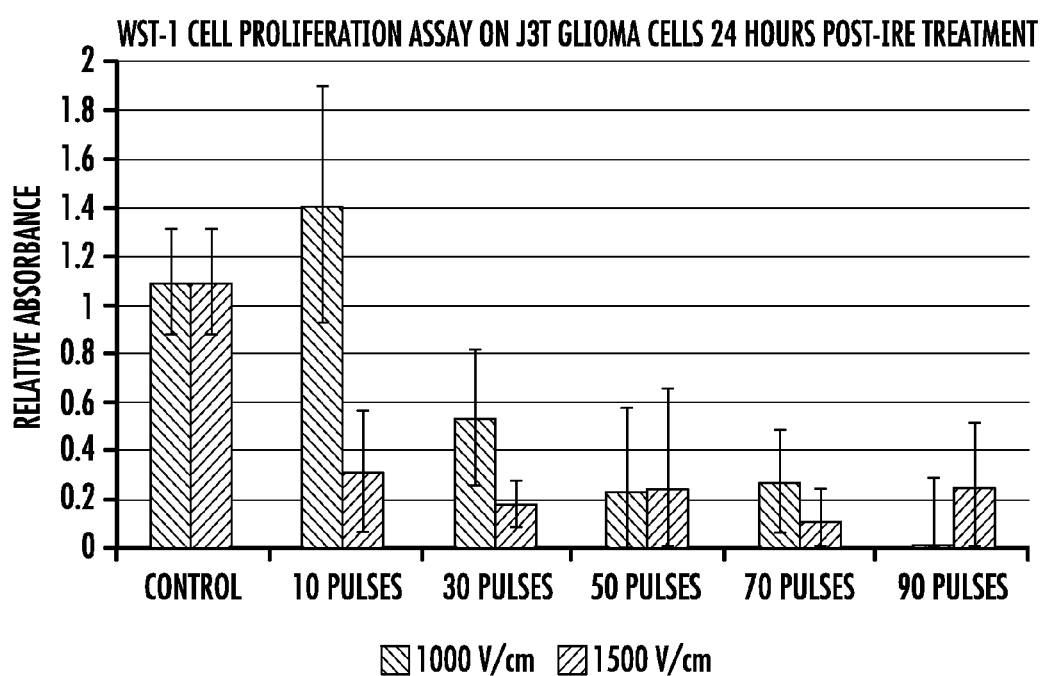
FIG. 6 shows a bar graph indicating results of IRE performed in vitro on J3T glioma cells at different pulse values.

As shown in FIG. 6, cell proliferation of canine glioma cells was significantly reduced or eliminated by treatment with IRE. More specifically, FIG. 1 shows the results of J3T glioma cells after treatment with electric pulses of length 50 microseconds (us) for 2 electric fields (1000 V/cm and 1500 V/cm) and multiple numbers of pulses. To develop the data shown in the figure, a WST-1 cell proliferation assay was performed on J3T glioma cells, and the data collected 24 hours post-IRE treatment. Two electric fields (1000 and 1500 V/cm) at 5 different pulse combinations were analyzed. A value of relative absorbance of 0.2 represents 100% cell death. Therefore, it is clear that for as low as 1000V/cm at 50 pulses total will achieve complete cell death for 50 us length pulses, proving this a viable IRE treatment parameter.

Example 3

Modeling of Electrode Shape and Placement

The present invention provides simple and elegant minimally invasive microsurgical tools to treat currently inoperable tumors in humans and animals through IRE. Exemplary designs are shown in FIGS. 7-11.

FIG. 7, Panel A, depicts an example of a device 700 according to one embodiment of the invention. This embodiment is fully compatible with existing electroporation electronics and comprises a surgical probe/electrode tip 710 at its distal end, which includes both ground electrodes 711 and energized electrodes 712. The device further comprises a universal connector 750 at its proximal end. The device also comprises internal wiring 770 to deliver electrical impulses to the tip 710. The body of the device is defined by surface 718.

The size and shape of the IRE area is dictated by the voltage applied and the electrode configuration and is readily predictable through numerical modeling. Therefore, different surgical tips can be fashioned to achieve the same therapeutic result. For example, tip 710 can comprises retractable conductive spikes 713 emanating from a blunt end tip 710 and disposed, when deployed, at an acute angle to tip 710 (see FIG. 7, Panel B). Alternatively, tip 710 can be fashioned as a point or needle, and can include retractable accordion-type conductive elements 714 (see FIG. 7, Panel C). In other exemplary embodiments, tip 710 can comprise multiple retractable spikes 715 that, when deployed, emanate at 90° C. from tip 710 (see FIG. 7, Panel D). Yet again, tip 710 can comprise retractable conductive spikes 716 emanating from a needle-end tip 710 and disposed, when deployed, at an acute angle to tip 710 (see FIG. 7, Panel E). FIG. 7, Panels B, D, and E, show probes with parallel circular channels 717 of approximately 1 mm that protrude through the length of the electrode holder. Each channel has the capability of guiding individual 1 mm electrodes to the treatment area. Towards the bottom of the holder, the channels deviate from their straight path at a specific angle. The electrodes can be Platinum/Iridium with an insulating polyurethane jacket to ensure biocompatibility, similar to materials that are used in DBS implants. Different protrusion depths of the electrodes within the tissue as well as the applied voltage can be used to control the size of the treated area.

The devices can comprise interchangeable surgical tips, allowing for versatility in creating a device well suited for different tissues or different sized or shaped tumors. Varying electrode diameters (varied in part by selection of the type and length of deployable spikes) and separation distances will be sufficient to ablate the majority of tumors about or smaller than 3 cm by selecting the appropriate voltages to match different tumor sizes and shapes. As shown in later figures, some of the embodiments of the device comprise an element at the tip to introduce anti-cancer drugs for ECT, cytotoxic proteins, or other bioactive agents into the targeted area.

While not depicted in detail, embodiments of the device comprise durable carbon coatings over portions of the device that act both to insulate normal tissue and to increase the efficiency of IRE pulsing.

With general reference to FIG. 7, Panels A-D, in brain tumor IRE treatment, for example, a single blunt-end device with embedded active and ground electrodes can be used. In an embodiment not particularly depicted in the figures, the device contains a primary blunt-end tip with a hole disposed in the end, for insertion through delicate, soft brain tissue. The device of these embodiments further comprises a secondary sharp tip, which can be deployed through the hole in the blunt-end primary tip, which allows for penetration into the tumor tissue, which can be substantially more dense or hard, and not easily punctured by a blunt-end tip. In general, the device of the invention is typically similar in dimensions (2 mm) to those already used in deep brain stimulation (DBS), which ensures that they are feasible for surgical applications. DBS uses electrodes in an FDA approved therapy to alleviate the symptoms of otherwise treatment-resistant disorders, such as Parkinson's disease and dystonia. Furthermore, the electrode positioning frame, which is used in stereotactic surgery in conjunction with imaging systems, can be used to position the surgical probes and ensure that the position of the electrodes is optimal. Simulations of a design similar to the one in FIG. 7A show treatment volumes comparable to typical brain tumors.

Figure 8A:
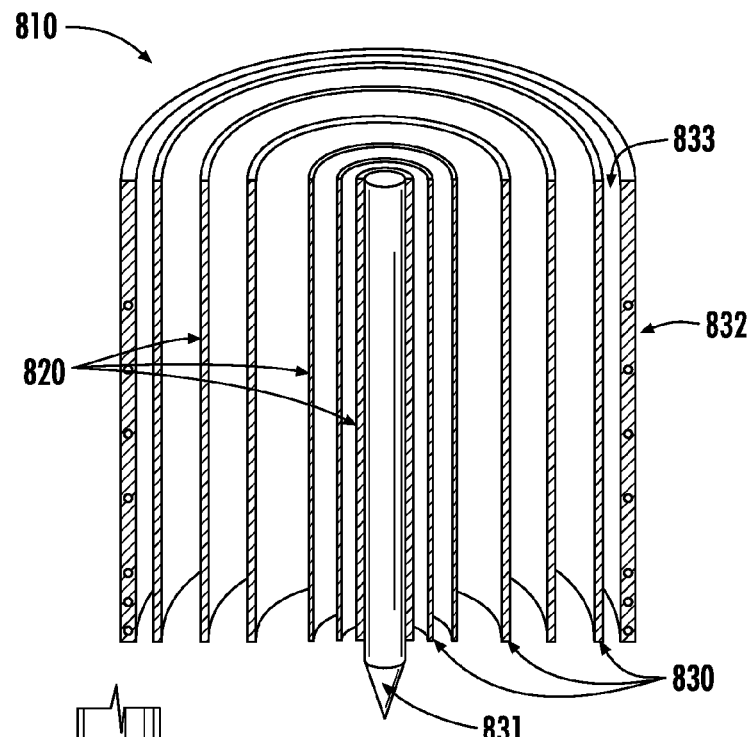
FIGS. 8A-C are schematic drawings showing an expanded view of an electrode tip according to one embodiment of the invention. Panel A depicts an exploded view of the various concentric layers of materials making up the electrode tip. Panel B depicts a side view of the electrode of Panel A, showing the various layers in cut-away fashion. Panel C depicts the electrode tip viewed along the proximal-distal plane.
Figure 8B:
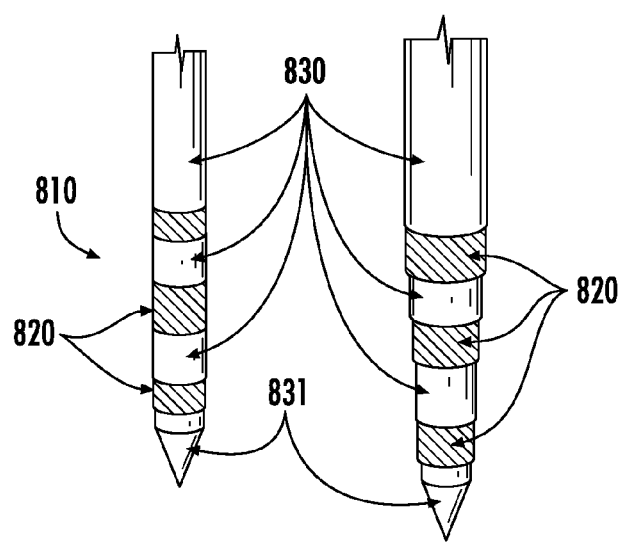
Figure 8C:

Turning now to FIG. 8, Panels A-C depict in more detail an embodiment of a tip 810 according to the invention. Panel A depicts an exploded view of tip 810, showing multiple concentric layers of conducting 820 and non-conducting 830 materials. An outer layer or sheath 860 of non-conducting material is shown with perforations 861. An outer, perforated layer 832 is disposed around the concentric rings of materials, to allow for delivery of bioactive substances to cells in proximity to the device when in use. Perforated layer 832 may be disposed in full, direct contact with the outermost layer of the concentric ring structure, or may be substantially separated from the ring structure by chamber 833 that holds cooling fluid.

As shown in the cut-away depiction in Panel B, device tip 810 has multiple alternating layers of conducting 820 and non-conducting 830 materials surrounding an non-conducting inner core 831. In Panel B, the top and bottom conducting regions 820 are energized electrodes while the middle conducting region 820 is a ground electrode. The present invention provides the conducting and non-conducting (insulative) regions in varying lengths to fine tune electrical field generation. More specifically, using imaging techniques directed at the tumor to be treated, a surgeon can determine what type of electrical field is best suited for the tumor size and shape. The device can comprise one or more movable elements on the surface of the tip (not depicted) or can be designed such that one or more of the alternating conducting 820 or non-conducting 830 elements is movable. Through movement and setting of the outer element(s) or inner elements 820 or 830, the surgeon can configure the device to deliver a three-dimensional electrical killing field to suit the needs of the particular situation.

FIG. 8, Panel C, depicts the concentric laminate structure of tip 810, viewed from the distal end along the distal-proximal axis, showing again the laminate nature of the device.

In addition to changing charges, adapting the physical dimensions of the probe also allows flexibility in tailoring the treatment area to match the dimensions of the tumor. By altering the electrode parameters, including diameter, length, separation distance, and type, it is possible to conveniently tailor the treatment to affect only specific, targeted regions. In addition, developing an electrode capable of altering and adapting to these dimensional demands greatly enhances its usability and adaptability to treatment region demands.

Example 4

Hollow Core Device

Many IRE treatments may involve coupled procedures, incorporating several discrete aspects during the same treatment. One embodiment of the invention provides a device with a needle-like tip 910 with an incorporated hollow needle 990 with either an end outlet 991 (shown in Panel A) or mixed dispersion regions 961 (shown in Panel B). Such a configuration allows for highly accurate distribution of injectable solutions, including those comprising bioactive agents. Use of such a device limits the dose of treatment required as well as ensures the correct placement of the materials prior to, during, and/or after the treatment. Some of the possible treatment enhancers that would benefit from this technology are: single or multi-walled carbon nanotubes (CNTs); chemotherapeutic agents; conductive gels to homogenize the electric field; antibiotics; anti-inflammatories; anaesthetics; muscle relaxers; nerve relaxers; or any other substance of interest.

The schematics in FIG. 9 show two basic hollow needle designs that may be implemented to enhance solution delivery prior to, during, or after IRE treatment. They both have multiple conducting surfaces 920 that may act as charged electrodes, grounded electrodes, or electric resistors, depending on the treatment protocol. Panel A shows a hollow tip 910 for injection of agents at its end while Panel B has distributed pores 961 throughout for a more generalized agent distribution. As shown in Panel B, the pores are disposed in the non-conducting regions 930 of the device.

Irreversible Electroporation (IRE), a new minimally invasive technique we invented to treat tumors, can be enhanced using carbon nanotubes (CNTs). The technique can be used on a variety of tumors including liver, prostate, pancreatic adenocarcinoma and renal carcinoma. Focal ablation techniques, such as IRE, however, are not selective and thus cannot distinguish between healthy and cancerous cells. To overcome this limitation, nanoparticles can be incorporated into IRE therapy. Nanomaterials offer a potential means for energy focusing, because they present a toolset with a unique size range closely matching that of cells (1 to 1,000 nm), and substantial multi-functional capability. Some embodiments of nanoparticles exhibit a "lightning rod" effect when exposed to electric fields, amplifying the field at the nanoparticle's tip, thereby producing a significantly larger electric potential compared to its surroundings and reducing the possibility of sub-lethal joule heating. This localized amplification of electric fields could thus be used as a means to induce IRE from relatively small electric fields; residual adverse effects to surrounding tissue would subsequently be reduced. Targeting of nanoparticles through tumor specific antibodies to the desired tissue region will allow treatment up to and beyond the tumor margin using IRE, and offer the opportunity to lower the IRE applied field, thereby minimizing damage to surrounding, non-cancerous tissue during treatment. Integration of CNTs into IRE could more selectively localize the electric field and thermal profile to cancer cells through antibody targeting and more precisely control the induction of cell death and HSP expression.

When carbon nanotubes (CNTs) are immersed in an electric field, an induced dipole is generated that tends to align the axis of the CNT parallel to the electric field. Taking advantage of these effects can be used to reduce cell damage during treatment. For example, two sets of electric fields delivered subsequent to and at right angles to each other is a technique that can be used to align the CNTs and electroporate the cells. Under some circumstances, cells electroporated using CNTs may result in cells having a higher vitality than when electroporated without the use of CNTs. The use of CNTs injected into a region of tissue, with or without targeting antibodies, to mediate IRE for tumor ablation is another method covered by the present invention.

In N-TIRE therapy, the local electric field distribution dictates the treatment area. When electric field parameters are optimized, N-TIRE possesses a clear therapeutic advantage in that there is no induction of thermal injury in the ablated area, thereby preserving important tissue components such as the extracellular matrix, major blood vessels, myelin sheaths, and nerves. Since N-TIRE is a focal ablation technique, it does not selectively kill infiltrative cancer cells with the potential for re-growth and metastasis beyond the tumor margin without affecting the surrounding healthy cells. The ablation area can be enlarged without inducing joule heating and the selectivity of N-TIRE can be enhanced through the use of CNTs. Localized amplification of electric fields from CNTs could induce N-TIRE in adjacent cells from relatively small electric fields, without affecting healthy surrounding cells. Further, antibody targeting of CNTs to tumor cells could permit localized CNT-mediated electric field amplification at selected tumor cell membranes causing targeted cell death due to permanent membrane destabilization. Even further, it is advantageous to incorporate CNTs into N-TIRE protocols in order to simultaneously lower the voltage for N-TIRE and expand the treatable area.

Combinatorial CNT-mediated N-TIRE cancer therapies can include treatment of a number of cancers including prostate, liver, kidney, and pancreatic. Breast cancer is a particularly apt application since this combinatorial therapy can directly address the need of scar reduction and mitigate the likelihood of metastasis, which have proven in some circumstances to be helpful for improved treatment. Adapting N-TIRE treatments for breast carcinomas has several unique challenges. Among these are the diverse and dynamic physical and electrical properties of breast tissue. The fatty and connective tissues within the breast region surrounding a tumor have low water content, and thus significantly reduced electrical conductivity and permittivity than tumors. It has been shown that N-TIRE treatment area is highly predictable based on electric field distribution. CNTs will provide a means to raise the electric field magnitude within the tumor and increase N-TIRE treatment area in localized breast carcinomas.

Selective destruction of tumor cells with CNT-mediated N-TIRE therapy is dependent upon targeting CNTs to the tumor cells of interest. In physiological conditions, cells uptake folic acid across the plasma membrane using the folate carrier to supply the folate requirements of most normal cells. In contrast, folate receptor (FR), a high affinity membrane folate-binding protein, is frequently overexpressed in a wide variety of cancer cells. Since it is generally either absent or present at only low levels in most normal cells, the FR has been identified as not only a marker of cancers but also a potential and attractive target for tumor-specific drug delivery. Thus, bioconjugated nanoparticles, such as those conjugated with folic acid (FA-NP), can be synthesized and used as drug delivery tools for administering drugs into cancer cells.

Example 5

Devices Comprising Active Cooling

In embodiments, the device comprises a cooling system within the electrode to reduce the highly localized temperature changes that occur from Joule heating. During the electric pulses for IRE, the highest quantity of heat generation is at the electrode-tissue interface. By actively cooling (for example, via water flow) the electrode during the procedure, these effects are minimized. Further, cooling provides a heat sink for the nearby tissue, further reducing thermal effects. This allows more flexibility in treating larger tissue regions with IRE while keeping thermal effects negligible, providing a greater advantage for IRE over conventional thermal techniques. Cooling can be achieved by placement of one or more hollow chambers within the body of the device. The cooling chambers can be closed or open. Open chambers can be attached at the proximal end to fluid pumping elements to allow for circulation of the fluid (e.g., water) through the device during use.

Example 6

Movable Outer Sheath

Figure 10:
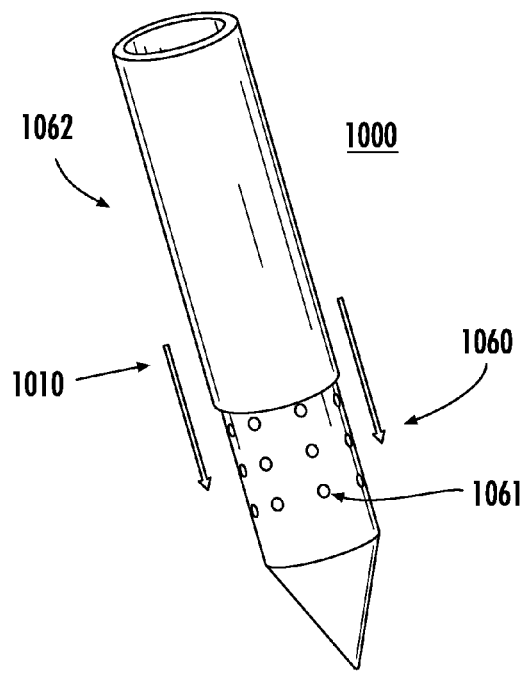
FIG. 10 depicts yet another embodiment of a device according to the invention, in which the outer, non-conductive sheath is adjustable to allow for selection of an appropriate depth/length of electrically conductive material to be exposed to tissue to be treated. The embodiment includes screw tappings (not shown) to allow real-time adjustment of the electrode layer lengths to customize electrode dimensions prior to a procedure.

In embodiments, the device comprises an outer protector that is designed to be movable up and down along the length of the device. FIG. 10 depicts such a movable outer protector. More specifically, FIG. 10 depicts a device 1000 comprising tip 1010 that includes outer protector 1062 that can be moved up and down along the length of device 1000. In practice, outer protector 1062 is disposed fully or partially encasing outer sheath 1060. After or during insertion into tissue to be treated, outer protector 1062 is retracted partially to expose outer sheath 1060, which in the embodiment depicted comprises mixed dispersion outlets 1061. As such, the number of dispersion outlets 1061 exposed to the tissue during treatment can be adjusted to deliver varying amounts of bioactive agent to different portions of the tissue being treated. Any mechanism for movement of the outer sheath along the device may be used. In embodiments, screw threads are disposed on the upper portion of the device, allowing for easy adjustment by simple twisting of the outer sheath. Alternatively, set screws may be disposed in the outer sheath, allowing for locking of the sheath in place after adjustment.

Example 7

System for IRE Treatment of Tumors

Figure 11:
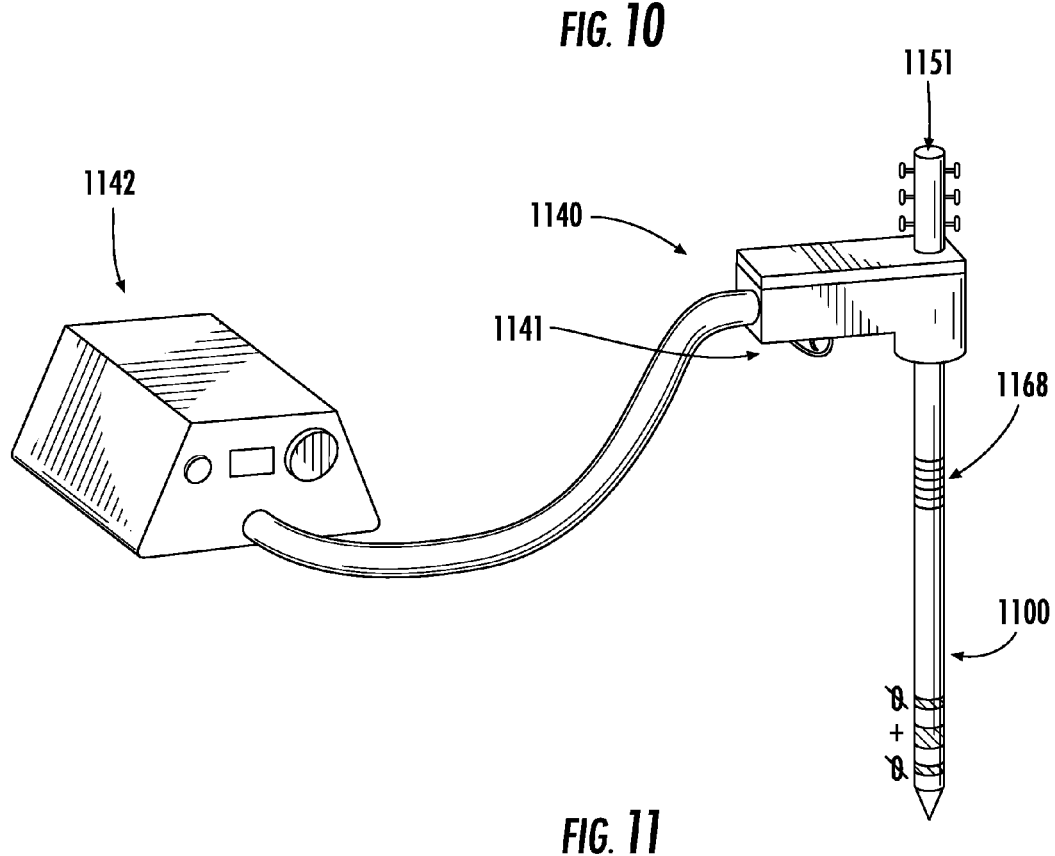
FIG. 11 depicts an exemplary system according to the invention, which includes an adjustable height electrode, a handle for physician guidance of the device into the patient, and a power source/controller to provide and control electrical pulses.

The invention provides a system for performing IRE tumor tissue ablation. As depicted in FIG. 11, an exemplary system can comprise a device 1100 reversibly attached to holder 1140. Holder 1140 can comprise trigger 1141, which allows the user to control the flow of electricity from power source/controller 1142 to device 1100.

In this embodiment, device 1100 comprises further elements for use. More specifically, device 1100 comprises a height adjustment apparatus 1151 at its proximal end to effect movement of outer sheath 1160. Outer sheath 1160 further comprises markings or scores 1168 on its surface to indicate amount of movement of outer sheath 1160 after implantation of device 1100 into tumor tissue.

Example 8

System for Controlling Multiple Electrodes

The invention provides a system for accurately controlling the distances between multiple electrodes of singular or multiple polarities during a charge. The device places electrode types within an adjustable part of a handle that may be maneuvered by a surgeon or attached to a harness system, as described above. The adjustable portion of the handle may be used to control the relative depths of penetration as well as separation distances of each electrode relative to one or more additional electrodes placed within the system.

Example 9

Modeling of Separation Distances Between Electrodes and Heat Generation

Figure 12E:
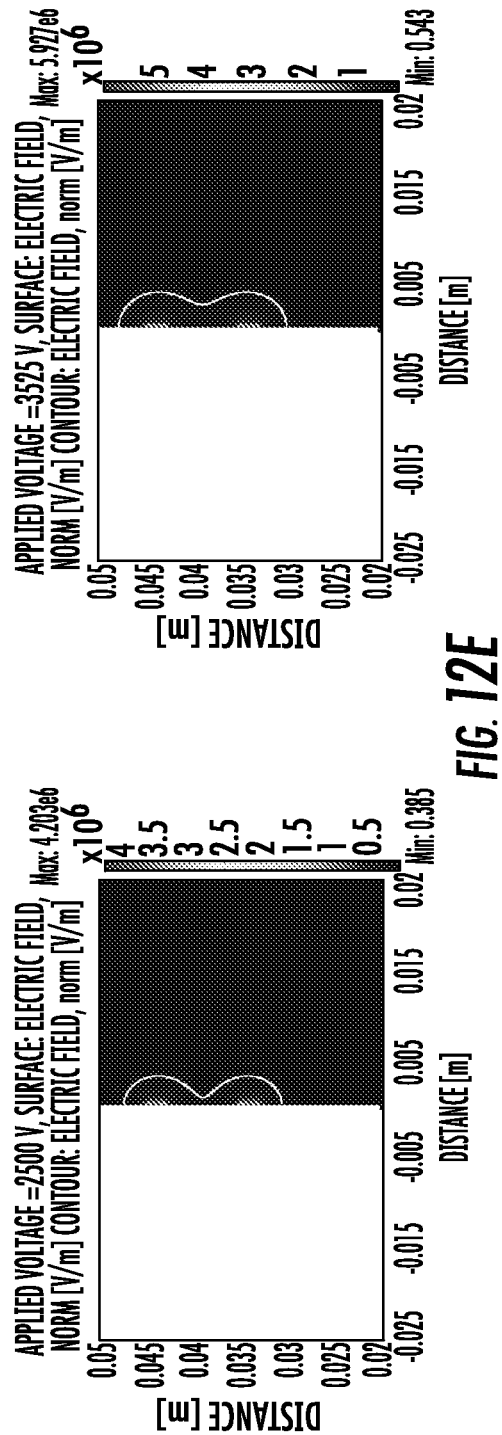

The system and method of the invention can include the use of multiple devices for treatment of tumors. The devices can be implanted in the tumor at varying distances from each other to achieve desired cell killing. Alternatively, the system and method can include the use of a single device having multiple electrodes along its tip. Modeling of placement of multiple devices or a single device with multiple electrodes in tissue was performed, and exemplary electrical fields generated are depicted in FIG. 12. The outputs depicted in the figure demonstrate the variability in IRE treatment region that results from altering the separation distance of the conducting electrode surfaces. More specifically, FIG. 12, Panels A-C, show three model outputs for 2-dimensional needles (left panels) and an axis symmetric electrode (right panels). For all images, there were two charged surfaces, one of 2500V and one of 0V. The distances between the electrodes were 0.5 cm (Panel A), 1.0 cm (Panel B), and 1.5 cm (Panel C). From this data, it is clear that altering the distance leads to significantly different electric field distributions, and thus makes the distance an important parameter to consider when developing IRE protocols for various tumor ablation.

Numerical models representing two needles and an axis symmetric needle electrode configuration have been developed to compare the increase in treatment area shown by the electric field distribution for the same thermal effects between 100 and 50 us pulse lengths. The area/volume of tissue that increased by at least 1 degree Kelvin was determined for a 100 us pulse. This area/volume was then used for the 50 us pulse to determine the electric field magnitude that would cause the same increase in temperature. A contour line has been created within these models to represent the region treated with the IRE threshold of 700V/cm. The results are shown in FIG. 12, Panel D. More specifically, 2-D needle electrodes with 3.13 mm$^2$ area of tissue increased by one degree Kelvin for 100 us pulse at 2500V/cm with 226.2 mm$^2$ area treated by IRE (Panel D, left side) and 50 us pulse at 3525V/cm with 325.6 mm$^2$ area affected by IRE (Panel D, right side). Axis symmetric needle electrode with 3.95 mm$^3$ volume of tissue increased by 1 degree Kelvin for 100 us at 1500V with 81.1 mm$^3$ volume affected by IRE (Panel E, left side) and 50 us pulse at 2120V with a 133 mm$^3$ volume within IRE range (Panel E, right side).

Example 10

Use of Different Tip Sizes

Figure 13A:
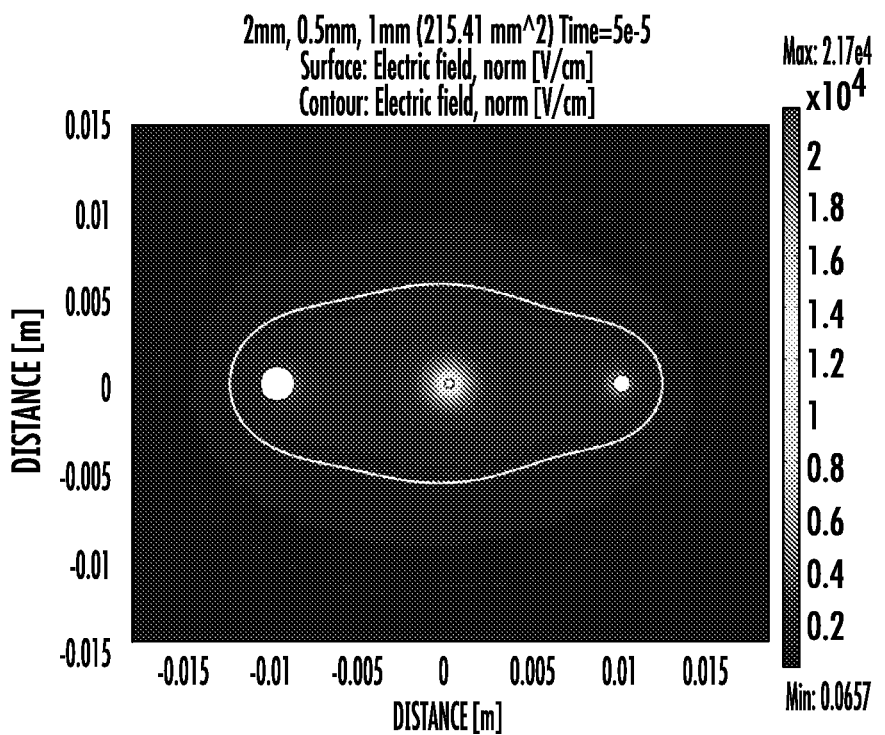
FIGS. 13A-C are electrical field outputs from various configurations employing three needle electrodes having different diameters. Panel A depicts the use of electrodes of 2 mm, 0.5 mm, and 1 mm (from left to right). Panel B depicts the use of electrodes of 2 mm, 1 mm, and 0.5 mm (from left to right). Panel C depicts the use of electrodes of 1 mm, 2 mm, and 0.5 mm (from left to right).
Figure 13B:
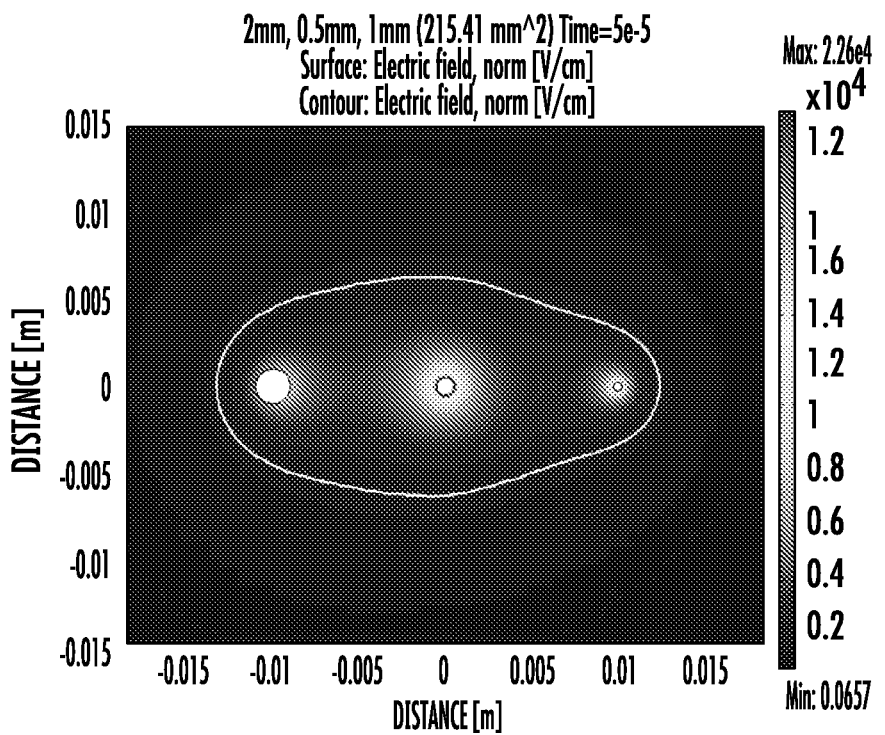
Figure 13C:
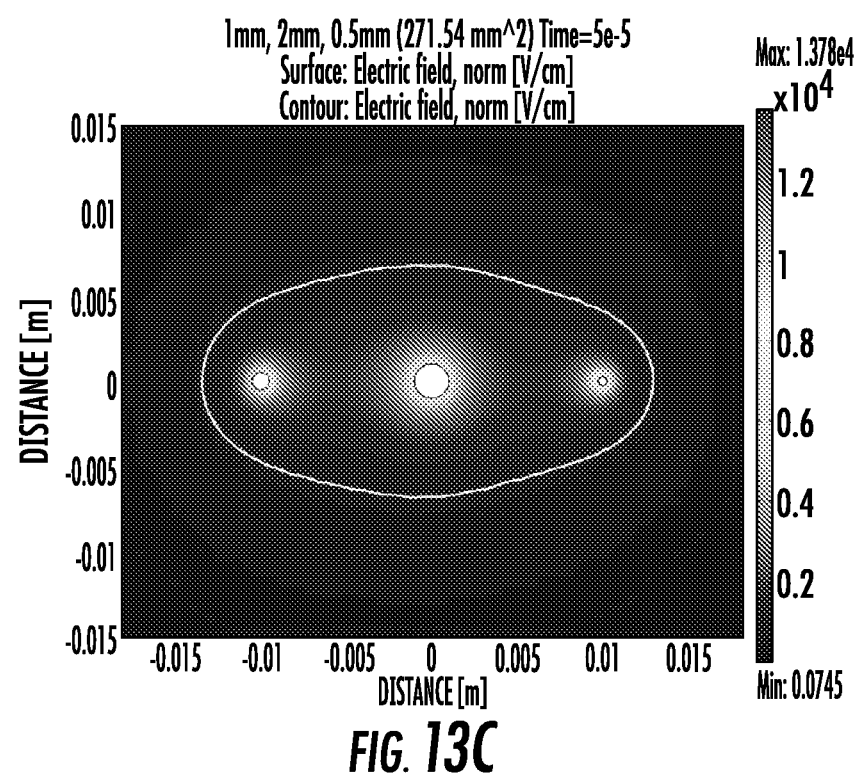
Figure 14A:
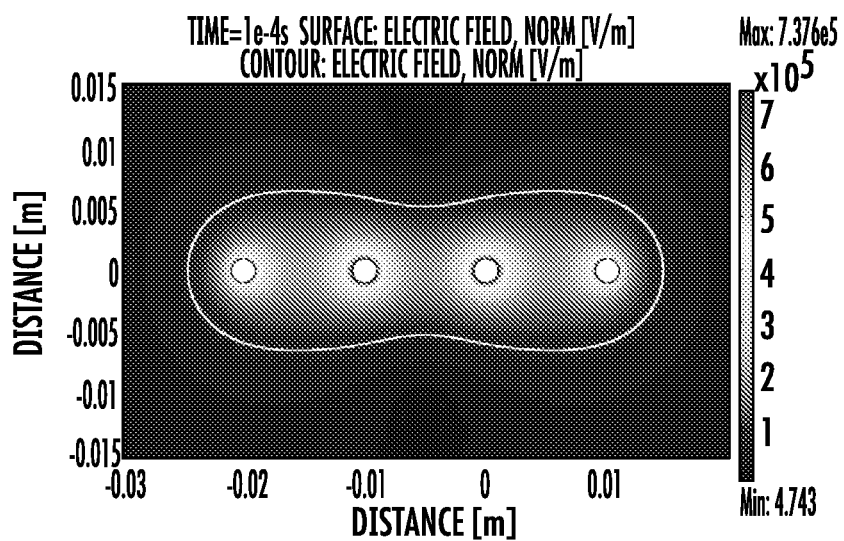
FIGS. 14A-J are electrical field outputs for various combinations of electrodes emitting different charges. Panel A depicts a two-dimensional display for the use of four electrodes of alternating polarity. Panel B depicts an axis symmetric display for the use of four similar electrodes of alternating polarity. Panel C depicts a two-dimensional display for the use of four charged electrodes, the center two at 5000V and 0V and the outer two at 2500V. Panel D depicts an axis symmetric display for the use of a similar electrode set up as Panel C. Panel E depicts a two-dimensional display for the use of three electrodes with the center one at 2500V and the outer two at 0V. Panel F depicts an axis symmetric display for the use of three electrodes similar to Panel E. Panel G depicts a two-dimensional display for the use of three charged electrodes, the center at 0V, the left at 5000V, and the right at 2500V. Panel H depicts an axis symmetric display for the use of a similar electrode set up as Panel G. Panel I depicts a two-dimensional display for the use of three charged electrodes, the center at 1750V, the left at 3000V, and the right at 0V. Panel J depicts an axis symmetric display for the use of a similar electrode set up as Panel I.
Figure 14B:
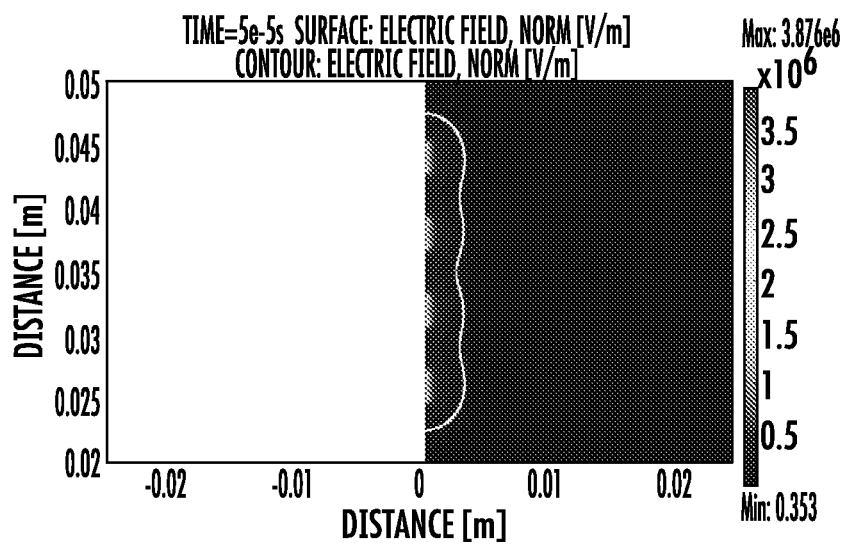
Figure 14C:
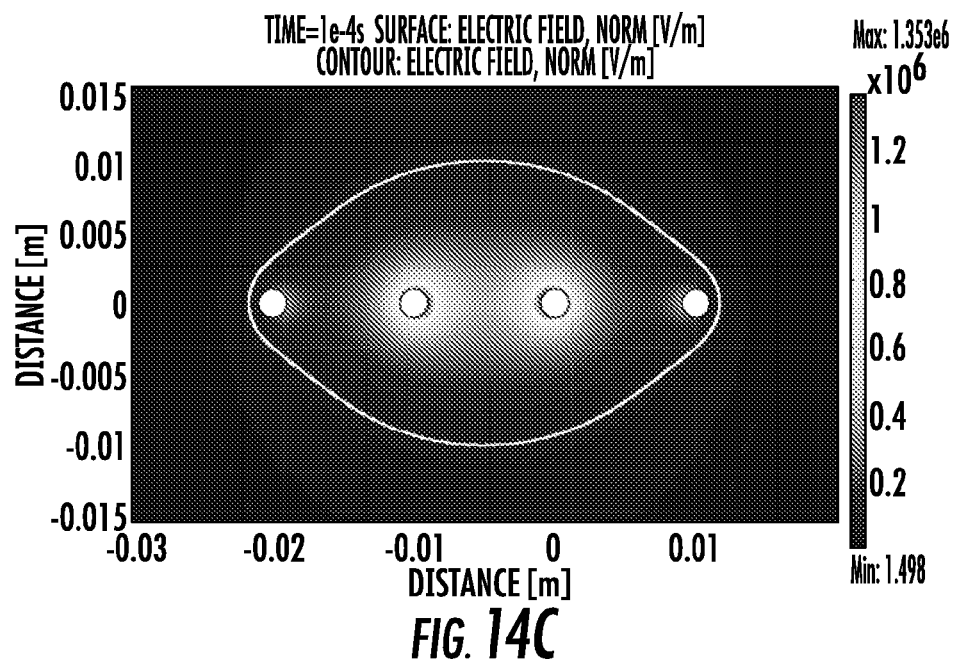
Figure 14D:
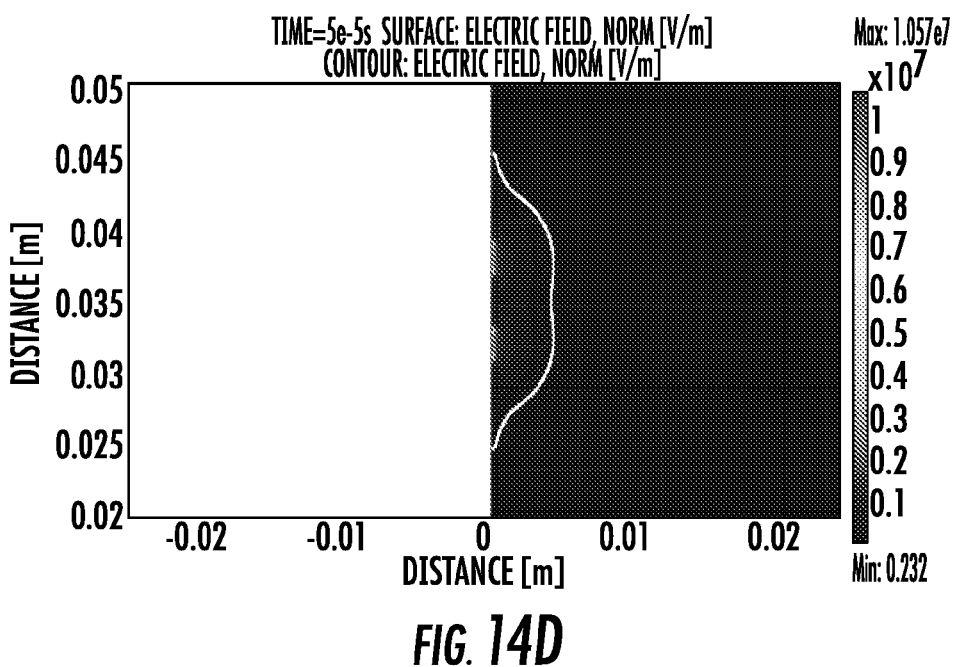
Figure 14E:
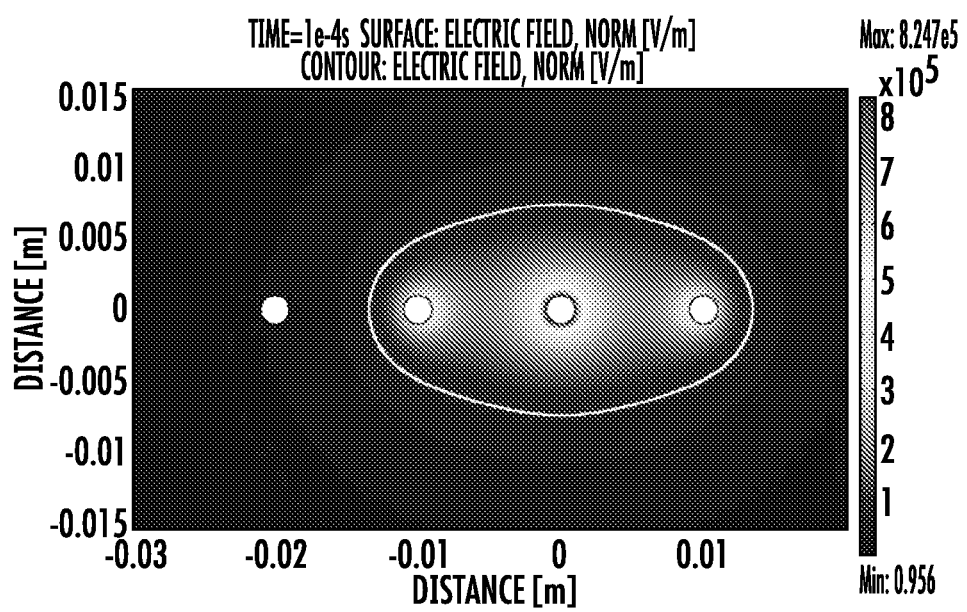
Figure 14F:
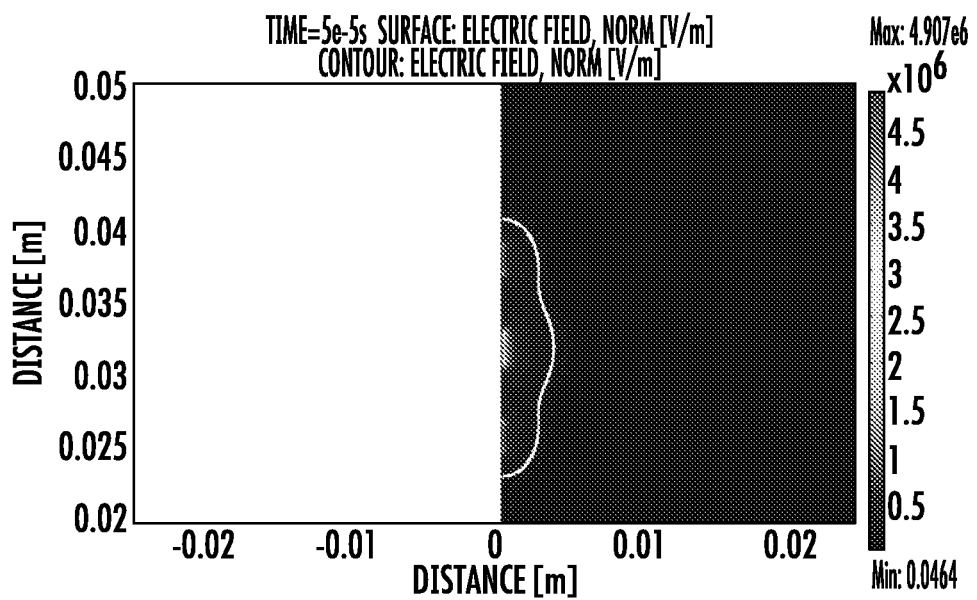
Figure 14G:
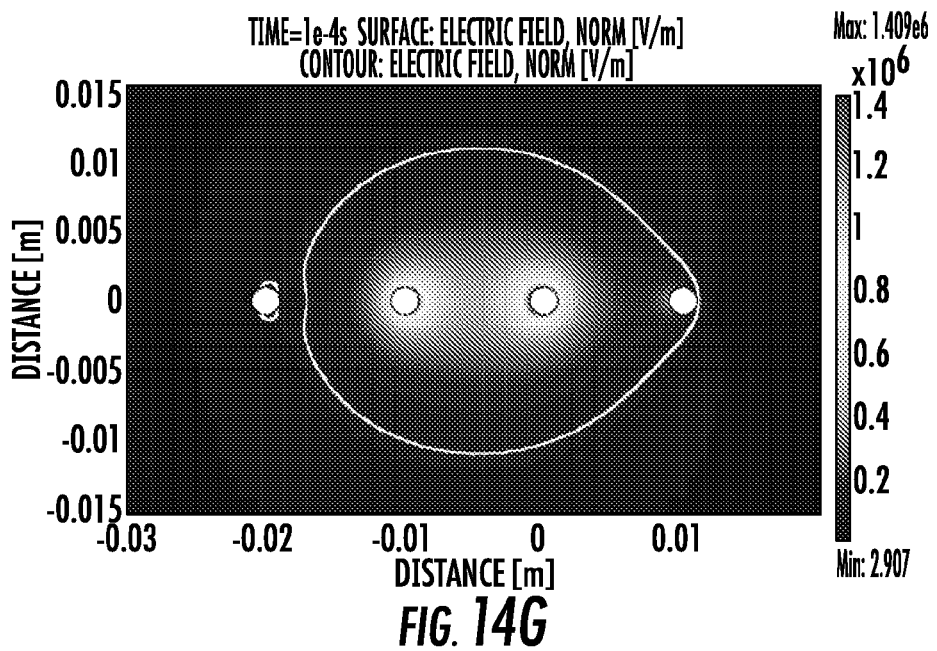
Figure 14H:
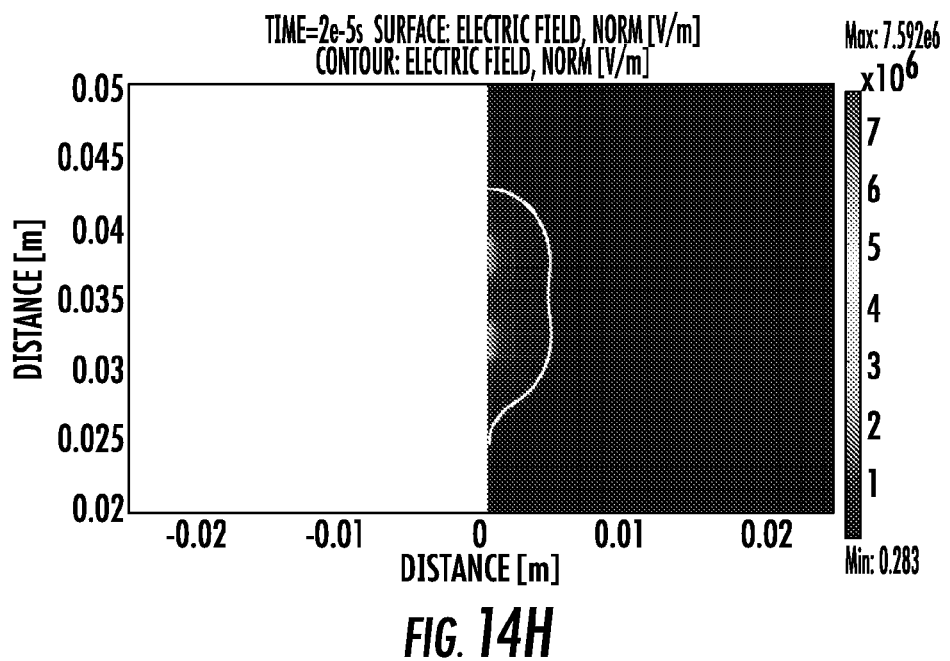
Figure 14I:
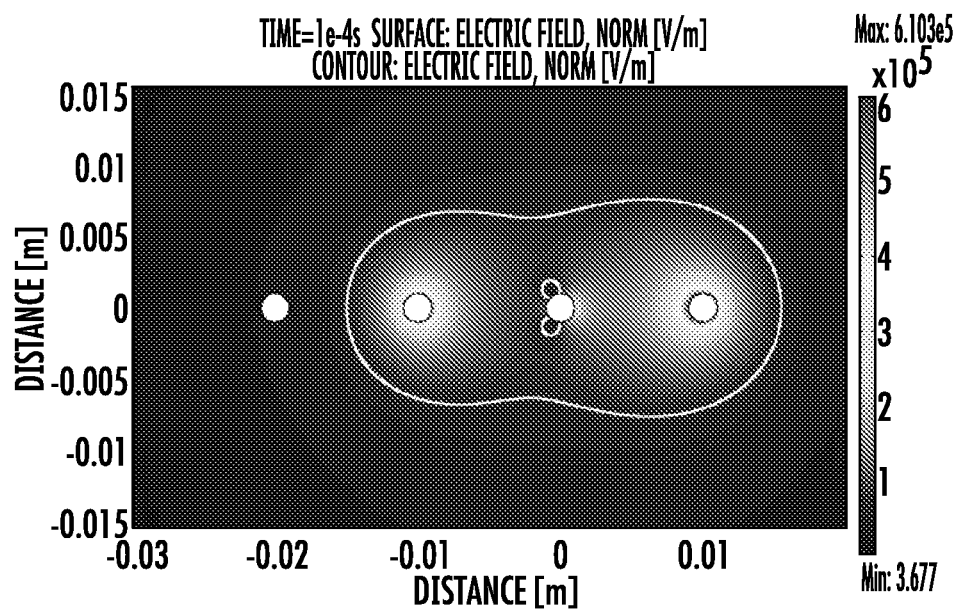
Figure 14J:
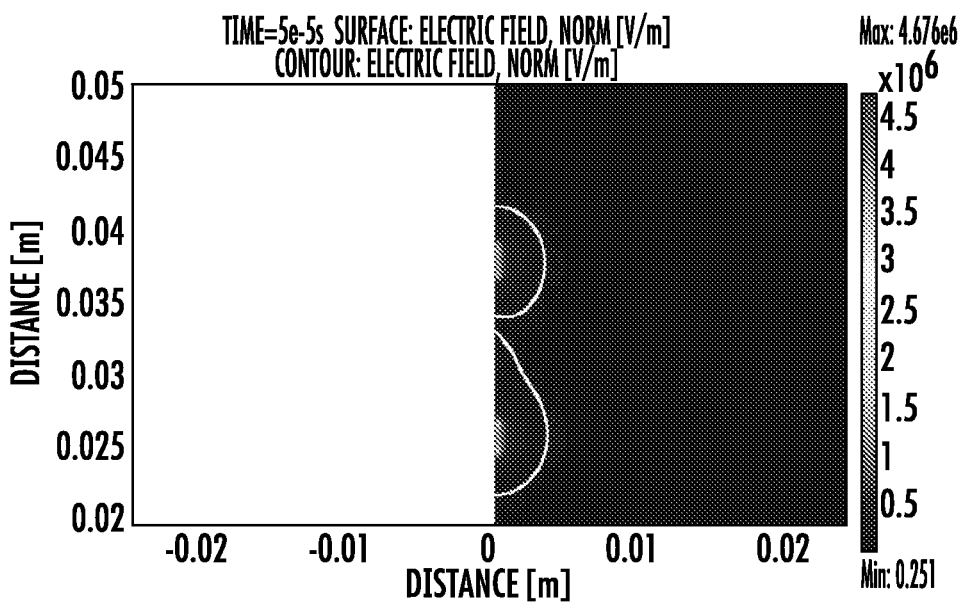
Figure 15A:
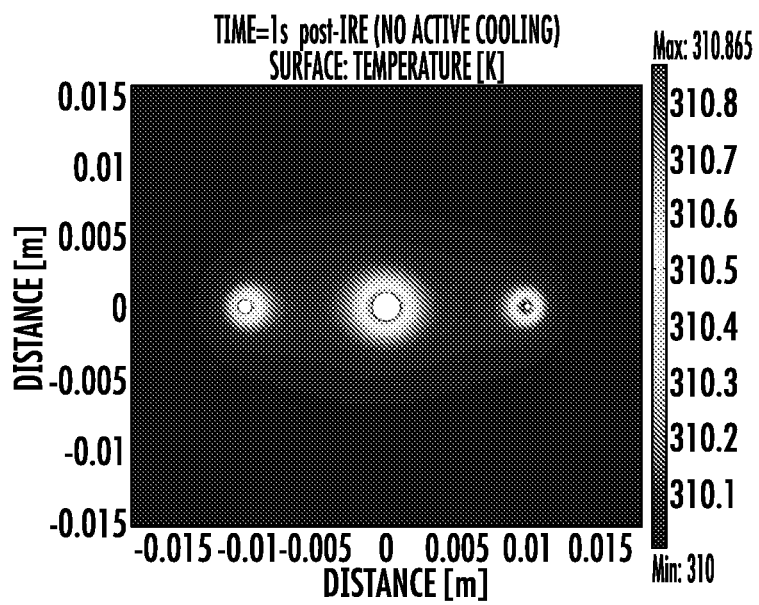
FIGS. 15A-D are schematics showing thermal effects from use of three needle electrodes, with and without use of a cooling element in the electrode. Panel A shows thermal effects without cooling, while Panel B shows the thermal effects under the same pulsing conditions, but with electrode cooling. Panel C shows thermal effects without cooling, while Panel D shows the thermal effects under the same pulsing conditions, but with electrode cooling.
Figure 15B:
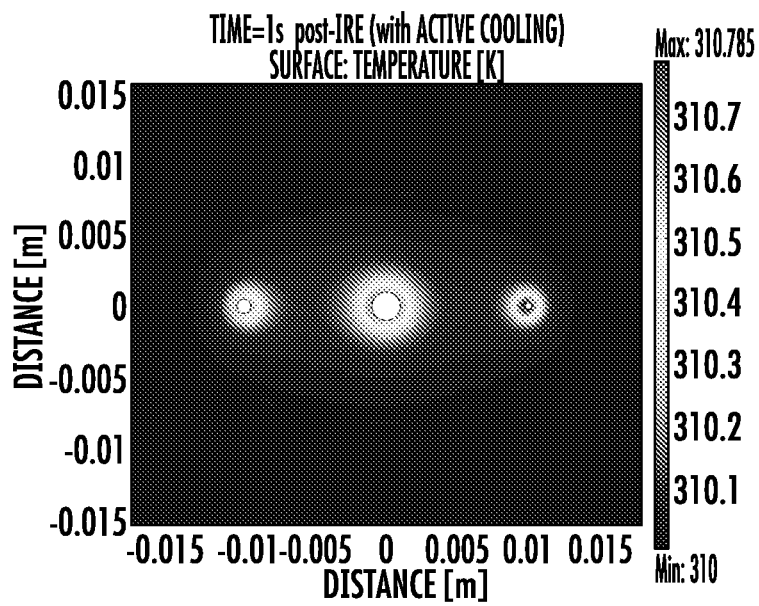
Figure 15C:
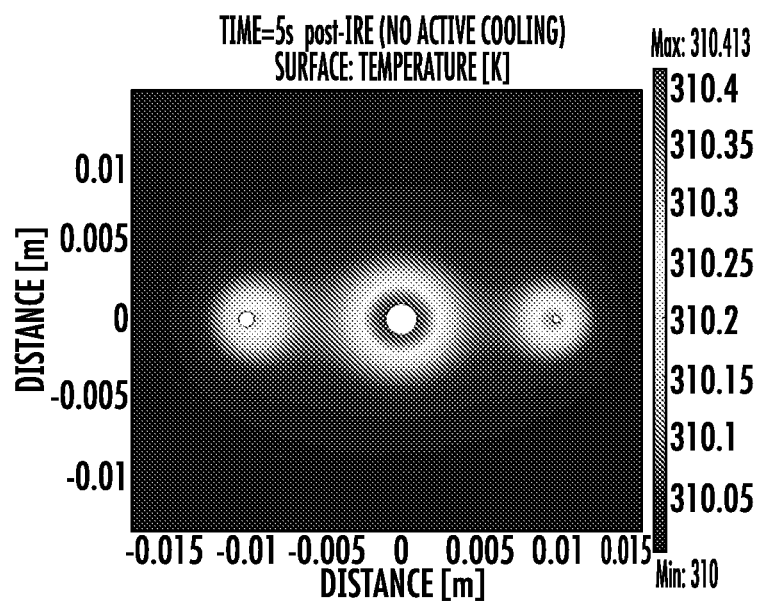
Figure 15D:
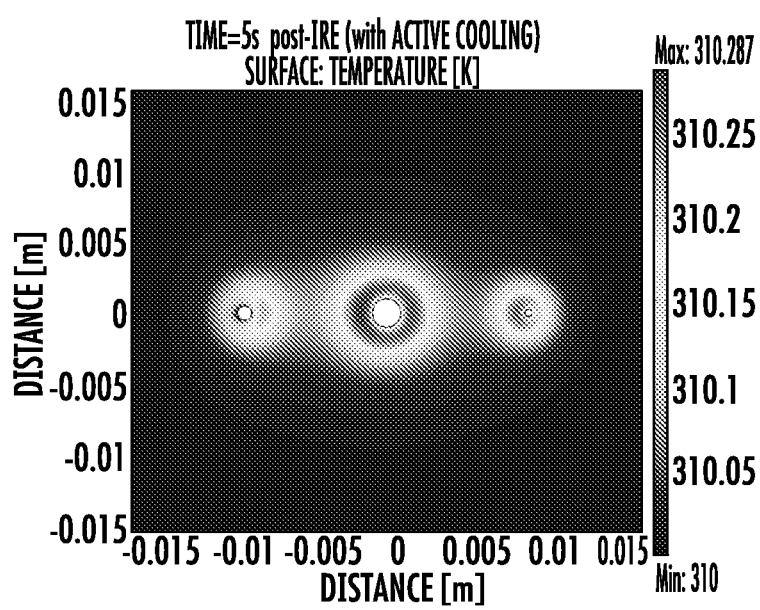

To provide exquisite control of electrical fields, and thus cell killing, the size of the electrode tips may be adjusted. In addition to real-time electrode manipulation capabilities, integrating multiple electrode types within the same procedure can make a large impact on enhancing electric field distribution selectivity. This can be done by incorporating such variations as a needle electrode with a single probe or parallel needle electrodes with the conductive surface of one being a different dimension (e.g., longer) than the other. As shown in FIG. 13, the electrical field output can be altered based on the arrangement of electrode types. More specifically, the figure shows model outputs displaying the electric field distribution for three needle electrodes, with a contour of 700V/cm. It can be seen that by mixing up the diameter of the electrodes (as displayed with each figure) within the same treatment, the shape and area of tissue treated by the 700V/cm threshold can be manipulated greatly. Panel A shows the use of tips having, from left to right, 2 mm diameter, 0.5 mm diameter, and 1 mm diameter, providing a 700V/cm threshold of 215.41 mm$^2$. Panel B shows the use of tips having, from left to right, 1 mm diameter, 1 mm diameter, and 0.5 mm diameter, providing a 700V/cm threshold of 243.26 mm$^2$. Panel C shows the use of tips having, from left to right, 1 mm diameter, 2 mm diameter, and 0.5 mm diameter, providing a 700V/cm threshold of 271.54 mm$^2$.

Example 11

Use of Multiple Electrode Charges

We have discovered that a highly customizable electric field distribution may be attained by combining multiple electrode charges within the same pulse. This allows a highly customized and controllable treatment protocol to match the dimensions of the target tissue. In addition, the invasiveness of the treatment may be decreased by reducing the number of electrode placements required for treatment. In order to demonstrate the great flexibility in electric field distribution shape, 2-dimensional and axis symmetric models were developed with 3 and 4 electrode arrays along a single axis. The results are depicted in FIG. 14, Panels A-D. For development of the data, only the electric potentials of the electrodes were manipulated to achieve the great flexibility needed in IRE treatment planning. For Panels A and B, four charged electrodes of alternating polarity at 2500V and ground were used to develop a 2-D readout (Panel A) and axis symmetric electrode configurations (Panel B). Four charged electrodes with the center two at 5000V and 0V and the outer two electrodes at 2500V were used to develop a 2-D readout (Panel C) and axis symmetric electrode configurations (Panel D). Three charged electrodes with the center one at 2500V and the outer two at 0V were used for 2-D (Panel E) and axis symmetric electrode (Panel F) configurations. Three charged electrodes with the center at 0V, left electrode at 5000V, and right electrode at 2500V for 2-D (Panel G) and axis symmetric (Panel H) scenarios. Three charged electrodes with the center at 1750V, left electrode at 3000V and right electrode at 0V for 2-D (Panel I) and axis symmetric electrode (Panel J) configurations.

Example 12

Thermal Effects for Long Duration Treatment

FIG. 15, Panels A-D display the modeling outputs of thermal effects during a typical IRE treatment, but for extended treatment periods. The images in Panels A and C display the thermal effects without convective cooling, while the images in Panels B and D have the same treatment parameters, but incorporate convective cooling of the needle. Panels A and B: IRE treatment with 3 needles (1 second post-IRE) without (Panel A) and with (Panel B) convective cooling at the electrode-tissue interface. It can be seen, particularly on the large center electrode that the temperature of the tissue contacting the electrode is the region of highest temperature without cooling, but is actually a lower temperature than the peripheral regions of the tissue. Panels C and D: IRE treatment with 3 needles (5 seconds post-IRE) without (Panel C) and with (Panel D) convective cooling at the electrode-tissue interface. It can be seen, particularly on the large center electrode, that the temperature of the tissue contacting the electrode is the region of highest temperature without cooling, but is actually a lower temperature than the peripheral regions of the tissue.

Example 13

Altering the Diameter and Shape of Electrodes

Figure 16A:
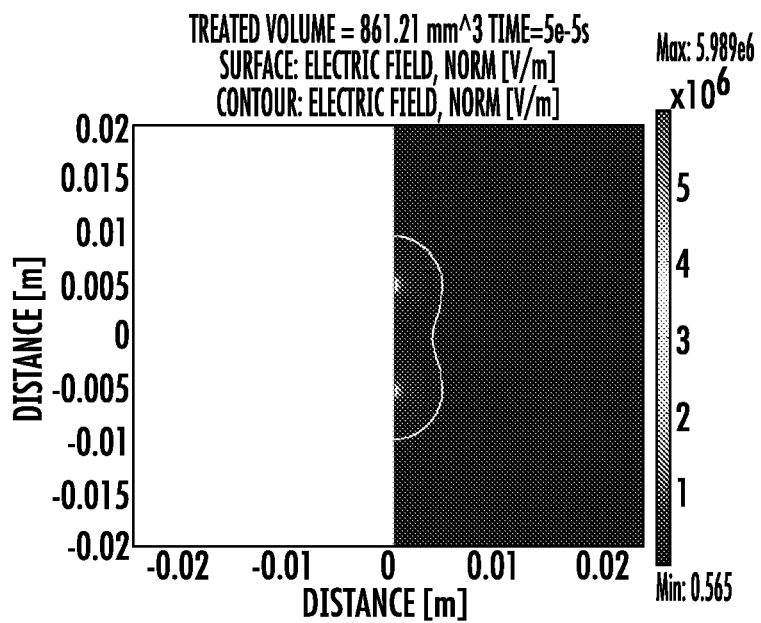
FIGS. 16A-C are schematics showing thermal effects from use of two bipolar electrodes and an intervening balloon.
Figure 16B:
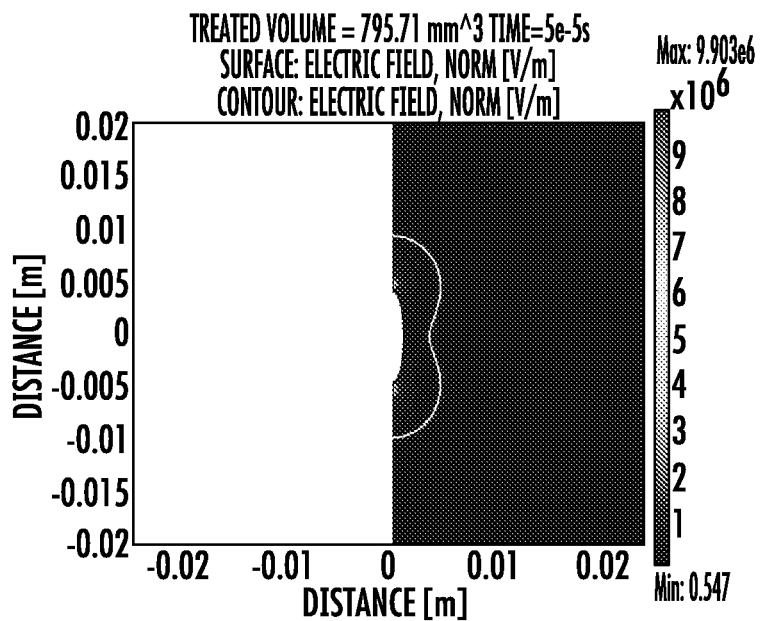
Figure 16C:
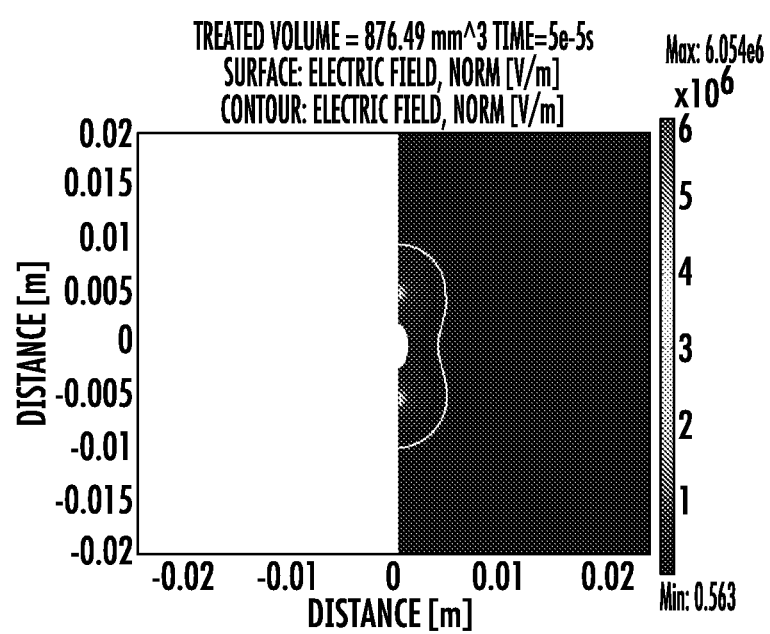

We have done some preliminary studies and determined that the electric field distribution may be altered, and thus controlled, by changing the diameter and shape of the electrode between the conducting surfaces. This fact can be used to design and develop an electrode with an expandable/contractible interior and deformable exterior to change its size in real-time before or during a treatment to alter, and thus specify the electric field distribution in a manner that may be desirable during treatment. The ability to adjust this dimension in real-time is made additionally useful by the fact that a significantly smaller electrode may be inserted to keep it minimally invasive, and then expand the dimension once the electrode has reached the target tissue. In embodiments, the invention includes the use of a balloon between regions of charge that may be inflated/deflated during treatment to alter field distribution. FIG. 16, Panels A-C, depict modeling of a bulging region between the charges in a bipolar electrode. Three different models that study the inclusion of a balloon between the two electrodes in a bipolar design are shown. Panel A (861.21 mm$^3$ treated area) has no balloon for comparison purposes. The middle design of Panel B (795.71 mm$^3$ treated area) has an elongated balloon that is in close proximity to the electrodes. The bottom design of Panel C (846.79 mm$^3$ treated area) has a smaller balloon that helps distribute the electric field.

Example 14

Alternating Polarity

With the application of electric potentials, electrical forces may drive ions towards one electrode or the other. This may also lead to undesirable behavior such as electrolysis, separating water into its hydrogen and oxygen components, and leading to the formation of bubbles at the electrode-tissue interface. These effects are further exacerbated for multiple pulse applications. Such effects may cause interference with treatment by skewing electric field distributions and altering treatment outcomes in a relatively unpredictable manner. By altering the polarity between the electrodes for each pulse, these effects can be significantly reduced, enhancing treatment predictability, and thus, outcome. This alternating polarity may be a change in potential direction for each pulse, or occur within each pulse itself (switch each electrode's polarity for every pulse or go immediately from positive to negative potential within the pulse at each electrode).

Example 15

Bipolar and Monopolar Electrodes

Using a bipolar electrode with 4 embedded electrodes, one can use the middle two electrodes to inject a sinusoidal current (~1-5 mA) that is low enough in magnitude to not generate electroporation and measure the voltage drop across the remaining two electrodes. From this setup one can calculate the impedance of the tissue and gather the conductivity of the tissue which is needed for treatment planning. One can do this analysis in a dynamic form after each electroporation pulse. Conductivity increases as a function of temperature and electroporation; therefore, for accurate treatment predictions and planning, the dynamic conductivity is needed and we can use the bipolar or unipolar electrodes to map the conductivity distribution before IRE treatment and during to adjust the pulse parameters.

Example 16

Parameters

The following are parameters that can be manipulated within the IRE treatments discussed herein.
Pulse length: 5 us-1 ms
Number of pulses: 1-10,000 pulses
Electric Field Distribution: 50-5,000 V/cm
Frequency of Pulse Application: 0.001-100 Hz
Frequency of pulse signal: 0-100 MHz
Pulse shape: square, exponential decay, sawtooth, sinusoidal, alternating polarity
Positive, negative, and neutral electrode charge pulses (changing polarity within probe)

Multiple sets of pulse parameters for a single treatment (changing any of the above parameters within the same treatment to specialize outcome)

Electrode type
Parallel plate: 0.1 mm-10 cm diameter
Needle electrode(s): 0.001 mm-1 cm diameter
Single probe with embedded disk electrodes: 0.001 mm-1 cm diameter
Spherical electrodes: 0.0001 mm-1 cm diameter
Needle diameter: 0.001 mm-1 cm
Electrode length (needle): 0.1 mm to 30 cm
Electrode separation: 0.1 mm to 5 cm Example 17

Specific Conductivity

The methods used to model tissue ablation are similar to the ones described by Edd and Davalos for predicting IRE areas based on the electric field and temperature distribution in the tissue (Edd, J. F, et al., 2007, "Mathematical modeling of irreversible electroporation for treatment planning.", Technology in Cancer Research and Treatment., 6:275-286.) The methods are disclosed in Garcia et al., "Irreversible electroporation (IRE) to treat brain cancer." ASME Summer Bioengineering Conference, Marco Island, Fla., Jun. 25-29, 2008.

We have modeled a new electrode design for the application of IRE in brain tissue. According to our results, IRE can be an effective technique for minimally invasive brain tumor removal. The treatment does not induce substantial thermal effects in the brain, protecting the integrity of this organ, which is susceptible to small fluctuations in temperature. In an embodiment of the method of the invention, the method includes delivering electrical signal(s) through tissue to determine its electrical properties before administering IRE by monitoring the voltage and current. Following from that, one may apply intermittent and post-IRE pulse(s), which can be used to determine the success of the procedure and adjust IRE pulse parameters.

Specific conductivity can be important for treatment planning of irreversible electroporation (IRE). For many applications, especially when treating tumors in the brain, the volume (area) of IRE must be predicted to maximize the ablation of the tumorous tissue while minimizing the damage to surrounding healthy tissue. The specific electrical conductivity of tissue during an irreversible electroporation (IRE) procedure allows the physicians to: determine the current threshold; minimize the electric current dose; decrease the Joule heating; and reduce damage to surrounding healthy tissue. To measure the specific conductivity of tissue prior to an IRE procedure the physician must: establish the electrode geometry (shape factor); determine the physical dimensions of the tissue; apply a small excitation AC voltage signal (1 to 10 mV); measure the AC current response; calculate the specific conductivity ($\sigma$) using results from the prior steps. This procedure will not generate tissue damage (low amplitude AC signals) and will supply the physician (software) with the required information to optimize IRE treatment planning, especially in sensitive organs like the brain which is susceptible to high electrical currents and temperatures. Thus, the IRE procedure is well monitored and can also serve as a feedback system in between series of pulses and even after the treatment to evaluate the area of ablation.

Special Cases for electrode geometry:
Nomenclature (units in brackets):
$V_e$=voltage on the hot electrode (the highest voltage), [V]
$R_1$=radius of electrode with highest voltage (inner radius), [m]
$R_2$=radius at which the outer electrodes are arranged (outer radius), [m]
i=total current, [A]
L=length of cylindrical electrode, [m]
$\sigma$=electrical conductivity of tissue, [S/m]

Electrical conduction between a two-cylinder (needle) arrangement of length L in an infinite medium (tissue). It is important to note that this formulation is most accurate when $L \gg R_1$, $R_2$ and $L \gg w$. The electrical conductivity can be calculated from, $$\sigma = \frac{i \cdot S}{V_e}$$

where the shape factor (S) corresponding to the electrode dimensions and configuration is given by, $$\frac{2 \cdot \pi \cdot L}{\cosh^{-1}\left(\frac{4 \cdot w^2 - (2 \cdot R_1)^2 - (2 \cdot R_2)^2}{8 \cdot R_1 \cdot R_2}\right)}$$

The specific conductivity ($\sigma$) of the tissue can be calculated since the voltage signal ($V_e$) and the current responses (i) are known.

Explanation of electrical concepts: By using the bipolar electrode described in the priority document, one can apply a small excitation AC voltage signal (1 to 10 mV), $$V(t) = V_0 \sin(wt)$$

where V(t) is the potential at time t, $V_0$ is the amplitude of the excitation signal and w is the frequency in radians/s. The reason for using a small excitation signal is to get a response that is pseudo-linear since in this manner we can determine the value for the impedance indicating the ability of a system (tissue) to resist the flow of electrical current. The measured AC current (response) that is generated by the excitation signal is described by $$I(t) = I_0 \sin(wt + q)$$

where I(t) is the response signal, $I_0$ is the amplitude of the response ($I_0^1 V_0$) and q is the phase shift of the signal. The impedance (Z) of the system (tissue) is described by, $$Z = (V(t))/(I(t)) = (V_0 \sin(wt))/(I_0 \sin(wt+q)) = Z_0(\sin(wt)/(\sin(wt+q)))$$

It is important to note that the measurement of the response is at the same excitation frequency as the AC voltage signal to prevent interfering signals that could compromise the results. The magnitude of the impedance $|Z_0|$ is the electrical resistance of the tissue. The electrical resistivity (W m) can be determined from the resistance and the physical dimensions of the tissue in addition to the electrode geometry (shape factor). The reciprocal of the electrical resistivity is the electrical conductivity (S/m). Therefore, after deriving the electrical resistivity from the methods described above, the conductivity may be determined.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

The invention claimed is:
1. A method of treating a subject suffering from a brain tumor, said method comprising:
creating a skull defect to gain access to the brain tumor;
positioning through the skull defect at least one electrode in or adjacent the brain tumor, the electrode having a blunt tip to minimize damage of brain tissue during positioning, wherein the blunt tip has an opening;
deploying through the opening another electrode having a pointed tip adapted to pierce the tumor tissue,
causing multiple electrical pulses to be emitted from the positioned electrode into the tumor in an amount sufficient to cause irreversible electroporation of tissue cells of the brain tumor.
2. The method of claim 1, wherein the electrical pulses are each 50 microseconds or less.
3. The method of claim 1, wherein the electrical pulses are each 25 microseconds or less.
4. The method of claim 1, further comprising:
applying an excitation voltage signal to the tissue cells of the brain tumor prior to the step of causing multiple electrical pulses to be emitted from the electrode;
measuring an electrical response to the excitation voltage signal and determining specific conductivity of the tissue cells;
determining at least one pulse parameter based on the specific conductivity of the tissue cells.
5. The method of claim 4, wherein the step of applying at least one excitation voltage signal includes applying an AC voltage signal whose strength is insufficient to cause irreversible electroporation of the tumor tissue cells.
6. The method of claim 4, further comprising:
applying one or more test voltage signals during the step of causing multiple electrical pulses to be emitted from the positioned electrode; and
adjusting at least one pulse parameter based on the applied test voltage signals.
7. The method of claim 4, further comprising measuring the response to the excitation voltage signal at substantially the same frequency as the excitation frequency of the excitation voltage signal.
8. The method of claim 1, further comprising adjusting one or more electrically conductive regions of the electrode.
9. The method of claim 8, where the one or more electrically conductive regions of the electrode are adjusted in real-time.
10. The method of claim 1, further comprising cooling the positioned electrode while the multiple electrical pulses are emitted.
11. A method of treating a brain tumor of a living subject with IRE, said method comprising:
providing at least one pair of electrodes;
implanting at least one electrode into or adjacent the brain tumor of the subject,
performing a pulse protocol causing multiple electrical pulses to be emitted from the implanted electrode into the brain tumor to cause IRE of tissue cells in the brain tumor, wherein the pulse protocol includes delivery of a total charge to the brain tumor of less than about 22.5 mC per pair of electrodes, wherein the pulse protocol is based on determining specific conductivity of the tissue cells in the brain tumor.

12. The method of claim 11, wherein the current is monitored in real-time and, based on that monitoring, at least one pulse parameter is changed.
13. The method of claim 11, wherein the pulse protocol includes at least one pulse parameter that is at least one of voltage, pulse length, and number of pulses.
14. A method of treating a living subject suffering from a tumor, said method comprising:
implanting at least one electrode into or adjacent the tumor within the body of the subject,
applying at least one excitation voltage signal to the tumor and measuring the response,
determining specific conductivity ($\sigma$) from the response to the excitation voltage signal,
using the specific conductivity ($\sigma$) to determine at least one pulse parameter,
using the determined pulse parameter, causing multiple electrical pulses to be emitted from the implanted electrode into the tumor to cause irreversible electroporation of tissue cells in the tumor.
15. The method of claim 14, comprising limiting the total charge to the tumor to about 22.5 mC or less per pair of electrodes.
16. The method of claim 14, wherein the at least one pulse parameter is at least one of pulse voltage, pulse length and number of pulses.
17. The method of claim 14, wherein the step of applying at least one excitation voltage signal includes applying at least one non-electroporating electric pulse in the range of about 50 V/cm or less.
18. The method of claim 14, wherein the electrical pulses are each 50 microseconds or less.
19. The method of claim 14, wherein the electrical pulses are each 25 microseconds or less.
20. The method of claim 14, wherein the step of applying at least one excitation voltage signal includes applying an AC voltage signal whose strength is insufficient to cause irreversible electroporation of the tumor tissue cells.
21. The method of claim 14, further comprising:
applying one or more test voltage signals during the step of causing multiple electrical pulses to be emitted from the implanted electrode; and
adjusting at least one pulse parameter based on the applied test voltage signals.
22. The method of claim 21, wherein the one or more test voltage signals are applied using the positioned electrode.
23. The method of claim 14, further comprising measuring the response to the excitation voltage signal at substantially the same frequency as the excitation frequency of the excitation voltage signal.
24. The method of claim 14, wherein the step of implanting at least one electrode includes implanting the electrode having a blunt tip.
25. The method of claim 24, wherein the blunt tip has an opening, and the step of implanting includes deploying another electrode through the opening.
26. The method of claim 25, wherein the blunt tip has an opening, and the step of implanting includes deploying through the opening another electrode having a pointed tip adapted to pierce the tumor tissue.
27. The method of claim 14, further comprising adjusting one or more electrically conductive regions of the electrode.
28. The method of claim 14, further comprising cooling the implanted electrode while the multiple electrical pulses are emitted.
29. The method of claim 14, wherein the step of measuring the response includes measuring current.

30. The method of claim 14, further comprising delivering an anti-swelling agent to reduce edema.

31. The method of claim 14, further comprising:
establishing an electrode shape factor; and
determining physical dimensions of the tumor;
wherein the determining of the specific conductivity is based on the shape factor, physical dimensions of the tumor, and the response to the excitation voltage signal.

* * * * *